US012643860B2

(12) United States Patent
Schotes et al.

(10) Patent No.: US 12,643,860 B2
(45) **Date of Patent: *Jun. 2, 2026**

(54) ENANTIOSELECTIVE HYDROGENATION OF 4-SUBSTITUTED 1,2-DIHYDROQUINOLINES IN PRESENCE OF A CHIRAL IRIDIUM CATALYST

(71) Applicant: Bayer Aktiengesellschaft, Leverkusen (DE)

(72) Inventors: Christoph Schotes, Düsseldorf (DE); Dirk Eckart Brohm, Mettmann (DE); Johannes Schranck, Basel (CH)

(73) Assignee: BAYER AKTIENGESELLSCHAFT (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/334,675

(22) Filed: Sep. 19, 2025

(65) Prior Publication Data

US 2026/0015326 A1 Jan. 15, 2026

Related U.S. Application Data

(63) Continuation of application No. 17/041,907, filed as application No. PCT/EP2019/057423 on Mar. 25, 2019, now abandoned.

(30) Foreign Application Priority Data

Mar. 26, 2018 (EP) .................................... 18163963

(51) Int. Cl.

| | |
|---|---|
| ***C07D 215/08*** | (2006.01) |
| ***B01J 31/18*** | (2006.01) |
| ***B01J 31/22*** | (2006.01) |
| ***B01J 31/24*** | (2006.01) |

(52) U.S. Cl.

CPC .......... *C07D 215/08* (2013.01); *B01J 31/189* (2013.01); *B01J 31/2295* (2013.01); *B01J 31/2404* (2013.01); *B01J 31/2447* (2013.01); *B01J 2231/645* (2013.01); *B01J 2531/0205* (2013.01); *B01J 2531/827* (2013.01)

(58) Field of Classification Search

CPC ... C07D 215/08; B01J 31/189; B01J 31/2295; B01J 31/2404; B01J 31/2447; B01J 2231/645; B01J 2531/0205; B01J 2531/827

See application file for complete search history.

(56) References Cited

U.S. PATENT DOCUMENTS

| | | | | |
|---|---|---|---|---|
| 9,796,678 | B2 | 10/2017 | Takahashi | |
| 2017/0022162 | A1 | 1/2017 | Takahashi et al. | |
| 2021/0009521 | A1* | 1/2021 | Schotes | B01J 31/2404 |
| 2022/0306583 | A1* | 9/2022 | Schotes | C07D 215/12 |
| 2022/0324810 | A1 | 10/2022 | Schotes et al. | |

FOREIGN PATENT DOCUMENTS

| | | | |
|---|---|---|---|
| CN | 106103413 | A | 11/2016 |
| DE | 112015001290 | T5 | 12/2016 |
| EP | 0654464 | A1 | 5/1995 |
| EP | 2202236 | A1 | 6/2010 |
| EP | 3103789 | B1 | 10/2018 |
| JP | 2012513445 | A | 6/2012 |
| JP | 2013035837 | A | 2/2013 |
| WO | 2010072746 | A1 | 7/2010 |
| WO | 2011162397 | A1 | 12/2011 |
| WO | 2012084812 | A1 | 6/2012 |
| WO | 2015141564 | A1 | 9/2015 |
| WO | 2015197530 | A2 | 12/2015 |
| WO | 2015197530 | A3 | 3/2016 |

OTHER PUBLICATIONS

A. Baeza et al. Iridium-Catalyzed Asymmetric Hydrogenation of N-Protected Indoles, Chemistry—A European Journal, 2010, VL-16, IS-7, pp. 2036-2039 (Supporting Information). (Year: 2010).*

Baeza, A. et al, (2010). "Iridium-Catalyzed Asymmetric Hydrogenation of N-Protected Indoles" Chem. Eur. J. 16 (7): 2036-2039.

Drury, W.J. et al, (2004). "Synthesis of Versatile Chiral N,P Ligands Derived from Pyridine and Quinoline" Angew. Chem. Int. Ed. 43(1): 70-74.

International Search Report mailed May 2, 2019 for PCT Application No. PCT/EP2019/057423, filed Mar. 25, 2019, 5 pages.

Kaiser, S. et al. (2006). "Iridium Catalysts with Bicyclic Pyridine—Phosphinite Ligands: Asymmetric Hydrogenation of Olefins and Furan Derivatives," Angewandte Chemie 118(31): 5318-5321.

Wang, A. et al. (2008). "Enantio- and Diastereoselective Hydrogenation of Farnesol and O-Protected Derivatives: Stereocontrol by Changing the C=C Bond Configuration," Angew. Chem. Int. Ed. 47: 2298-2300.

Woodmansee, D. H. et al. (2010). "Chiral pyridyl phosphinites with large aryl substituents as efficient ligands for the asymmetric iridium-catalyzed hydrogenation of difficult substrates," Chemical Science, 1:72-78.

* cited by examiner

*Primary Examiner* — James H Alstrum-Acevedo
*Assistant Examiner* — Manahil Mirghani Ali Abdalhameed
(74) *Attorney, Agent, or Firm* — MORRISON & FOERSTER LLP

(57) ABSTRACT

The invention relates to a process for preparing optically active 4-substituted 1,2,3,4-tetrahydroquinolines comprising enantioselective hydrogenation of the corresponding 4-substituted 1,2-dihydroquinolines in presence of a chiral iridium (P,N)-ligand catalyst.

14 Claims, No Drawings

ENANTIOSELECTIVE HYDROGENATION OF 4-SUBSTITUTED 1,2-DIHYDROQUINOLINES IN PRESENCE OF A CHIRAL IRIDIUM CATALYST

CROSS REFERENCE TO RELATED APPLICATIONS

This application is a continuation of U.S. patent application Ser. No. 17/041,907, which adopts the international filing date of Mar. 25, 2019, which is a national stage application under 35 U.S.C. § 371 of International Application No. PCT/EP2019/057423, filed internationally on Mar. 25, 2019, which claims the benefit of priority to European Application No. 18163963.4, filed Mar. 26, 2018.

The invention relates to a process for preparing optically active 4-substituted 1,2,3,4-tetrahydroquinolines comprising enantioselective hydrogenation of the corresponding 4-substituted 1,2-dihydroquinolines in presence of a chiral iridium (P,N)-ligand catalyst.

It is known from EP 0 654 464 that N-acetyl-tetrahydroquinolines can be converted to the corresponding 4-aminoindane derivatives via a rearrangement reaction.

4-aminoindane derivatives are important intermediates for preparing various N-indanyl heteroaryl carboxamides having fungicidal activity (EP 0 654 464, WO 2011/162397, WO 2012/084812, WO 2015/197530).

EP 3 103 789 discloses a method for optically resolving 1,1,3-trimethyl-4-aminoindane by converting the enantiomeric mixture into the diastereomeric salts of D-tartaric acid. (R)- and (S)-1,1,3-trimethyl-4-aminoindane are obtained after separation and basification of the diastereomeric salts. This reference also discloses a method for racemizing the undesired enantiomer, so that the whole method allows for converting the undesired enantiomer into the desired enantiomer via several process steps. (R)-1,1,3-trimethyl-4-aminoindane is an important intermediate for preparing the pyrazole carboxamide fungicide inpyrfluxam.

A method for preparing chiral intermediates of N-indanyl heteroaryl carboxamides via asymmetric synthesis is also known. WO 2015/141564 describes a process for preparing optically active 4-substituted 1,2,3,4-tetrahydroquinolines, which process comprises the hydrogenation of the corresponding 4-substituted 1,2-dihydroquinolines in presence of a transition metal catalyst having an optically active ligand. The asymmetric hydrogenation of the 4-substituted NH-dihydroquinolines proceeded with moderate conversion rates (up to 62.6%) and enantioselectivity (up to 71.3% ee), whereas N-acetyl-dihydroquinolines gave even poorer conversion (up to 14%) and enantioselectivity (up to 31% ee).

In the light of the prior art described above, it is an object of the present invention to provide a process for preparing optically active 4-substituted 1,2,3,4-tetrahydroquinolines which process has advantages over the processes of the prior art. The process should allow the desired enantiomer to be prepared in high yield and high enantiomeric purity, with few process steps and few purification steps.

The object described above was achieved by a process for preparing a compound of the formula (Ia) or (Ib), (Ia)

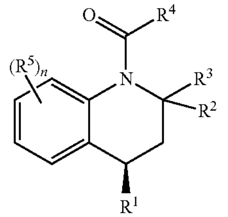

(Ib)

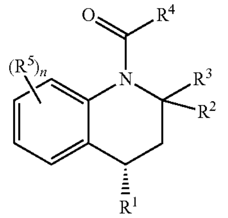

wherein $R^1$ is selected from the group consisting of $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_6$-$C_{14}$-aryl, or $C_6$-$C_{14}$-aryl-$C_1$-$C_4$-alkyl,
  wherein the $C_1$-$C_6$-alkyl, $C_3$-$C_6$-cycloalkyl and the $C_1$-$C_6$-alkoxy in the $C_1$-$C_6$-alkoxy-$C_1$-$C_6$-alkyl moiety, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and
  wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^2$ and $R^3$ are the same and are selected from the group consisting of hydrogen, $C_1$-$C_6$-alkyl, $C_1$-$C_6$-haloalkyl and $C_1$-$C_6$-alkoxy-$C_1$-$C_6$-alkyl, or $R^2$ and $R^3$ together with the carbon to which they are bonded, form a $C_3$-$C_6$-cycloalkyl ring, $R^4$ is hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_2$-$C_6$-alkenyloxy, 9-flurorenylmethyleneoxy, $C_6$-$C_{14}$-aryl, $C_6$-$C_{14}$-aryloxy, $C_6$-$C_{14}$-aryl-$C_1$-$C_4$-alkyloxy or $C_6$-$C_{14}$-aryl-$C_1$-$C_4$-alkyl,
  wherein the $C_6$-$C_{14}$-aryl as such or as part of a composite substituent is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, n is 0, 1, 2, 3 or 4, each substituent $R^5$, if present, is independently selected from the group consisting of halogen, $C_1$-$C_6$-alkyl, $C_1$-$C_6$-haloalkyl, $C_1$-$C_6$-alkoxy, hydroxyl, amino and $-C(=O)-C_1$-$C_6$-alkyl, comprising enantioselective hydrogenation of a compound of the formula (II)

(II)

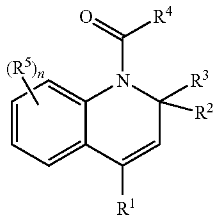

wherein the substituents $R^1$, $R^2$, $R^3$, $R^4$, $R^5$ and the integer n are each as defined for the compound of the formula (Ia) or (Ib), in presence of a chiral iridium catalyst, characterized in that the chiral iridium catalyst comprises a chiral ligand of the formula (IIIa), (IIIb), (IVa) or (IVb), (IIIa)

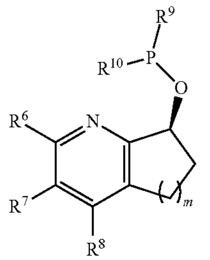

(IIIb)

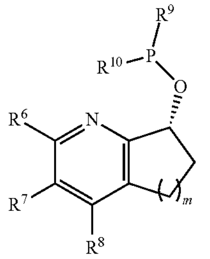

(IVa)

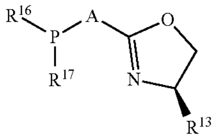

(IVb)

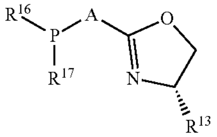

wherein $R^6$, $R^7$ and $R^8$ are independently from one another selected from the group consisting of hydrogen, halogen, $C_1$-$C_6$-alkyl, $C_1$-$C_6$-haloalkyl, $C_1$-$C_6$-alkoxy, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_6$-$C_{14}$-aryl and $C_6$-$C_{14}$-aryl-$C_1$-$C_4$-alkyl, wherein the $C_1$-$C_6$-alkyl, $C_2$-$C_6$-alkenyl, $C_2$-$C_6$-alkynyl, $C_3$-$C_7$-cycloalkyl and the $C_3$-$C_7$-cycloalkyl in the $C_3$-$C_7$-cycloalkyl-$C_1$-$C_4$-alkyl moiety are optionally substituted by 1 to 3 substituents independently selected from the group consisting of halogen, $C_1$-$C_4$-alkyl, $C_1$-$C_4$-alkoxy and $C_1$-$C_4$-haloalkyl and $C_1$-$C_4$-haloalkoxy, and wherein the $C_6$-$C_{14}$-aryl and the $C_6$-$C_{14}$-aryl in the $C_6$-$C_{14}$-aryl-$C_1$-$C_4$-alkyl moiety are optionally substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl again is unsubstituted or substituted by one to five $C_1$-$C_6$-alkyl substituents, $R^9$ and $R^{10}$ are independently from one another selected from the group consisting of $C_1$-$C_6$-alkyl, $C_2$-$C_6$-alkenyl, $C_2$-$C_6$-alkynyl, $C_1$-$C_6$-alkoxy, di($C_1$-$C_6$-alkyl)amino, $C_3$-$C_{12}$-cycloalkyl, $C_3$-$C_{12}$-cycloalkyl-$C_1$-$C_4$-alkyl, $C_6$-$C_{14}$-aryl, $C_6$-$C_{14}$-aryloxy and $C_6$-$C_{14}$-aryl-$C_1$-$C_4$-alkyl, wherein the $C_1$-$C_6$-alkyl, $C_2$-$C_6$-alkenyl, $C_2$-$C_6$-alkynyl, $C_1$-$C_6$-alkoxy and di($C_1$-$C_6$-alkyl)amino, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and wherein the $C_6$-$C_{14}$-aryl, $C_6$-$C_{14}$-aryloxy and $C_3$-$C_{12}$-cycloalkyl, in each case as such or as part of a composite substituent, are optionally substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl is unsubstituted or substituted by one to five $C_1$-$C_6$-alkyl substituents or $R^9$ and $R^{10}$ together with the phosphorus atom to which they are bonded, form a phospholane ring, which may be substituted with one or two $C_1$-$C_6$-alkyl groups, or $R^9$ and $R^{10}$ together form $G^1$ =

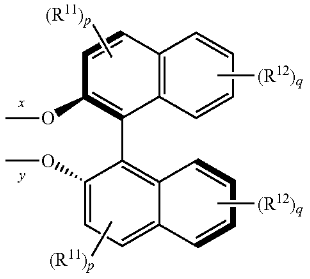

or $G^2$ =

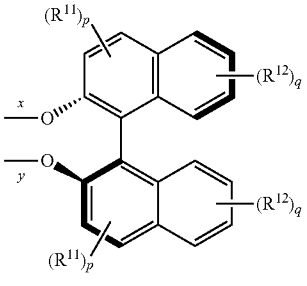

where the bonds identified by "x" and "y" are both bonded directly to the phosphorus atom, p and q are independently from one another selected from 0, 1 and 2, $R^{11}$ and $R^{12}$ are independently selected from $C_1$-$C_6$-alkyl and phenyl, which may be substituted by one to five substituents selected from the group consisting of halogen, $C_1$-$C_4$-alkyl, $C_1$-$C_4$-alkoxy and phenyl, which may be substituted by one or two $C_1$-$C_4$-alkyl substituents, m is 1 or 2, A is $A^1$ = 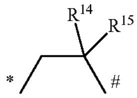 or $A^2$ = 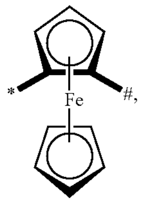

where the bond identified by "*" is bonded directly to the phosphorus atom and where the bond identified by "#" is bonded directly to the oxazoline moiety, $R^{13}$ is $C_1$-$C_6$-alkyl, $C_1$-$C_6$-haloalkyl, $C_3$-$C_{12}$-cycloalkyl, $C_3$-$C_{12}$-cycloalkyl-$C_1$-$C_4$-alkyl, $C_1$-$C_4$-alkyl-$C_3$-$C_7$-cycloalkyl, $C_6$-$C_{14}$-aryl or $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{14}$ and $R^{15}$ are independently from one another selected from the group consisting of hydrogen, $C_1$-$C_6$-alkyl, $C_1$-$C_6$-haloalkyl, $C_3$-$C_{12}$-cycloalkyl, $C_3$-$C_7$-cycloalkyl-$C_1$-$C_4$-alkyl, $C_1$-$C_4$-alkyl-$C_3$-$C_7$-cycloalkyl, $C_6$-$C_{14}$-aryl and $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{14}$ and $R^{15}$ together with the carbon to which they are bonded, form a $C_5$-$C_6$-cycloalkyl ring, $R^{16}$ and $R^{17}$ are independently from one another selected from the group consisting of $C_1$-$C_6$-alkyl, $C_2$-$C_6$-alkenyl, $C_2$-$C_6$-alkynyl, $C_1$-$C_6$-alkoxy, di($C_1$-$C_6$-alkyl)amino, $C_3$-$C_{12}$-cycloalkyl, $C_3$-$C_{12}$-cycloalkyl-$C_1$-$C_4$-alkyl, $C_6$-$C_{14}$-aryl, $C_6$-$C_{14}$-aryloxy and $C_6$-$C_{14}$-aryl-$C_1$-$C_4$-alkyl, wherein the $C_1$-$C_6$-alkyl, $C_2$-$C_6$-alkenyl, $C_2$-$C_6$-alkynyl, $C_1$-$C_6$-alkoxy, $C_1$-$C_6$-cycloalkyl and di($C_1$-$C_6$-alkyl)amino, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, phenyl, $C_1$-$C_4$-alkoxy, $C_1$-$C_4$-haloalkyl, and $C_1$-$C_4$-haloalkoxy, and wherein the $C_6$-$C_{14}$-aryl, the $C_6$-$C_{14}$-aryl in the $C_6$-$C_{14}$-aryl-$C_1$-$C_4$-alkyl, the $C_6$-$C_{14}$-aryloxy and $C_3$-$C_{12}$-cycloalkyl, in each case as such or as part of a composite substituent, are optionally substituted by one to five substituents selected from the group consisting of halogen, $C_1$-$C_4$-alkyl, phenyl, $C_1$-$C_4$-haloalkyl, $C_1$-$C_4$-alkoxy and $C_1$-$C_4$-haloalkoxy, or $R^{16}$ and $R^{17}$ together with the phosphorus atom to which they are bonded, form a phospholane ring, which may be substituted with one or two $C_1$-$C_6$-alkyl groups, or $R^{16}$ and $R^{17}$ together form $G^1$ = 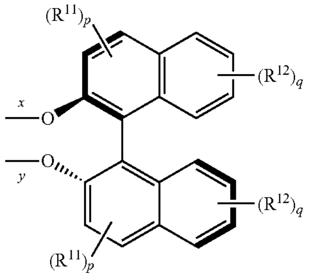 or $G^2$ = 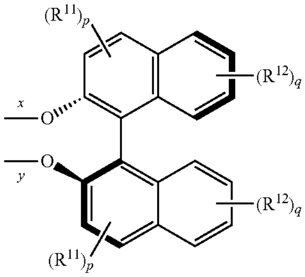

where the bonds identified by "x" and "y" are both bonded directly to the phosphorus atom, p and q are independently from one another selected from 0, 1 and 2, and $R^{11}$ and $R^{12}$ are independently selected from $C_1$-$C_6$-alkyl and phenyl, which may be substituted by one to five substituents selected from the group consisting of halogen, $C_1$-$C_4$-alkyl, $C_1$-$C_4$-alkoxy and phenyl, which may be substituted by one or two $C_1$-$C_4$-alkyl substituents.

It has been found, surprisingly, that optically active 4-substituted 1,2,3,4-tetrahydroquinolines (Ia and Ib) can be prepared in high yields and excellent enantioselectivity by enantioselective hydrogenation of the corresponding 4-substituted 1,2-dihydroquinolines (II) in presence of a chiral iridium (P,N)-ligand catalyst.

Definitions

In the definitions of the symbols given in the above formulae, collective terms were used, which are generally representative of the following substituents:

Halogen: fluorine, chlorine, bromine or iodine, preferably fluorine, chlorine or bromine, and more preferably fluorine or chlorine.

Alkyl: saturated, straight-chain or branched hydrocarbyl substituents having 1 to 6, preferably 1 to 4 carbon atoms, for example (but not limited to) $C_1$-$C_6$-alkyl such as methyl, ethyl, propyl (n-propyl), 1-methylethyl (iso-propyl), butyl (n-butyl), 1-methylpropyl (sec-butyl), 2-methylpropyl (iso-butyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2, 2-trimethylpropyl, 1-ethyl-1-methylpropyl and 1-ethyl-2-methylpropyl. Particularly, said group is a $C_1$-$C_4$-alkyl group, e.g. a methyl, ethyl, propyl, 1-methylethyl (isopropyl), butyl, 1-methylpropyl (sec-butyl), 2-methylpropyl (iso-butyl) or 1,1-dimethylethyl (tert-butyl) group. This definition also applies to alkyl as part of a composite substituent, for example $C_3$-$C_6$-cycloalkyl-$C_1$-$C_4$-alkyl, $C_6$-$C_{14}$-aryl-$C_1$-$C_4$-alkyl etc., unless defined elsewhere.

Alkenyl: unsaturated, straight-chain or branched hydrocarbyl substituents having 2 to 6, preferably 2 to 4 carbon atoms and one double bond in any position, for example (but not limited to) $C_2$-$C_6$-alkenyl such as vinyl, allyl, (E)-2-methylvinyl, (Z)-2-methylvinyl, isopropenyl, homoallyl, (E)-but-2-enyl, (Z)-but-2-enyl, (E)-but-1-enyl, (Z)-but-1-enyl, 2-methylprop-2-enyl, 1-methylprop-2-enyl, 2-methylprop-1-enyl, (E)-1-methylprop-1-enyl, (Z)-1-methylprop-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, (E)-3,3-dimethylprop-1-enyl, (Z)-3,3-dimethylprop-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-cnyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl. (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, 1-(1,1-dimethylethyl)ethenyl, buta-1,3-dienyl, penta-1,4-dienyl, hexa-1,5-dienyl or methylhexadienyl. Particularly, said group is vinyl or allyl. This definition also applies to alkenyl as part of a composite substituent unless defined elsewhere.

Alkynyl: straight-chain or branched hydrocarbyl substituents having 2 to 8, preferably 2 to 6, and more preferably 2 to 4 carbon atoms and one triple bond in any position, for example (but not limited to) $C_2$-$C_6$-alkynyl, such as ethynyl, prop-1-ynyl, prop-2-ynyl, but-1-ynyl, but-2-ynyl, but-3-ynyl, 1-methylprop-2-ynyl, pent-1-ynyl, pent-2-ynyl, pent-3-ynyl, pent-4-ynyl, 2-methylbut-3-ynyl. 1-methylbut-3-ynyl, 1-methylbut-2-ynyl, 3-methylbut-1-ynyl, 1-ethylprop-2-ynyl, hex-1-ynyl, hex-2-ynyl, hex-3-ynyl, hex-4-ynyl, hex-5-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl. This definition also applies to alkynyl as part of a composite substituent unless defined elsewhere.

Alkylamino: monoalkylamino or dialkylamino, wherein monoalkylamino represents an amino radical having one alkyl residue with 1 to 4 carbon atoms attached to the nitrogen atom. Non-limiting examples include methylamino, ethylamino, n-propylamino, isopropylamino, n-butylamino and tert-butylamino. Wherein dialkylamino represents an amino radical having two independently selected alkyl residues with 1 to 4 carbon atoms each attached to the nitrogen atom. Non-limiting examples include N,N-dimethylamino, N,N-diethyl-amino, N,N-diisopropylamino, N-ethyl-N-methylamino, N-methyl-N-n-propylamino, N-isopropyl-N-n-propylamino and N-tert-butyl-N-methylamino.

Alkoxy: saturated, straight-chain or branched alkoxy substituents having 1 to 6, more preferably 1 to 4 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent unless defined elsewhere.

Cycloalkyl: mono- or polycyclic, saturated hydrocarbyl substituents having 3 to 12, preferably 3 to 8 and more preferably 3 to 6 carbon ring members, for example (but not limited to) cyclopropyl, cyclopentyl, cyclohexyl and adamantyl. This definition also applies to cycloalkyl as part of a composite substituent, for example $C_3$-$C_6$-cycloalkyl-$C_1$-$C_4$-alkyl, unless defined elsewhere.

Haloalkyl: straight-chain or branched alkyl substituents having 1 to 6, preferably 1 to 4 carbon atoms (as specified above), where some or all of the hydrogen atoms in these groups are replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluorocthyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy substituents having 1 to 6, preferably 1 to 4 carbon atoms (as specified above), where some or all of the hydrogen atoms in these groups are replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, unless defined elsewhere.

Aryl: mono-, bi- or tricyclic aromatic or partially aromatic substituents having 6 to 14 carbon atoms, for example (but not limited to) phenyl, naphthyl, tetrahydronapthyl, indenyl and indanyl. The binding to the superordinate general structure can be carried out via any possible ring member of the aryl residue. Aryl is preferably selected from phenyl, 1-naphthyl, 2-naphthyl, 9-phenantryl und 9-antracenyl. Phenyl is particularly preferred.

The term "enantioselective" as used herein means that one of the two possible enantiomers of the hydrogenation product, namely the enantiomer of the formula (Ia) or the enantiomer of the formula (Ib), is preferably formed. The "enantiomeric excess" or "ee" indicates the degree of enantioselectivity:

$$\%\ ee = \frac{\text{major enantiomer (mol)} - \text{minor enantiomer (mol)}}{\text{major enantiomer (mol)} + \text{minor enantiomer (mol)}} \times 100\%$$

The major enantiomer can be controlled by the selection of the chiral ligand, for example by selecting the chiral ligand of the formula (IIIa) or the opposite enantiomer (the ligand of the formula (IIIb)), or respectively by selecting the chiral ligand of the formula (IVa) or the opposite enantiomer (the ligand of the formula (IVb)).

The process according to the invention is used for preparing the compound of the formula (Ia) or (Ib), preferably (Ia).

Preferred are compounds of the formula (Ia) or (Ib), in particular (Ia), wherein the substituents are defined as follows:

$R^1$ is $C_1$-$C_6$-alkyl or $C_6$-$C_{14}$-aryl-$C_1$-$C_4$-alkyl,
wherein $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy
$R^2$ and $R^3$ are the same and are selected from $C_1$-$C_4$-alkyl,
$R^4$ is $C_1$-$C_4$-alkyl, $C_1$-$C_4$-haloalkyl, $C_1$-$C_4$-alkoxy, $C_1$-$C_4$-haloalkoxy, phenyl or benzyl,
n is 0, 1 or 2,
each substituent $R^5$, if present, is independently selected from the group consisting of halogen, $C_1$-$C_6$-alkyl and $C_1$-$C_6$-haloalkyl.

More preferred are compounds of the formula (Ia) or (Ib), in particular (Ia), wherein the substituents are defined as follows:

$R^1$ is $C_1$-$C_6$-alkyl
$R^2$ and $R^3$ are the same and are selected from $C_1$-$C_4$-alkyl,
$R^4$ is $C_1$-$C_4$-alkyl, $C_1$-$C_4$-haloalkyl, phenyl or benzyl,
n is 0, 1 or 2,
each substituent $R^5$, if present, is independently selected from the group consisting of halogen and $C_1$-$C_6$-alkyl.

Even more preferred are compounds of the formula (Ia) or (Ib), in particular (Ia), wherein the substituents are defined as follows:

$R^1$ is methyl, ethyl or n-propyl,
$R^2$ and $R^3$ are methyl,
$R^4$ is $C_1$-$C_4$-alkyl,
n is 0, 1 or 2,
each substituent $R^5$, if present, is independently selected from the group consisting of halogen and $C_1$-$C_6$-alkyl.

Most preferred are compounds of the formula (Ia) or (Ib), in particular (Ia), wherein the substituents are defined as follows:

$R^1$ is methyl or n-propyl,
$R^2$ and $R^3$ are methyl,
$R^4$ is methyl,
n is 0 or 1,
substituent $R^5$, if present, is fluorine.

The process according to the invention comprises enantioselective hydrogenation of the compound of the formula (II). The substituents $R^1$, $R^2$, $R^3$, $R^4$, $R^5$ and the integer n in the compound of the formula (II) are each as defined for the compound of the formula (Ia) or (Ib).

The enantioselective hydrogenation of the compound of the formula (II) is conducted in presence of a chiral iridium catalyst comprising a chiral ligand of the formula (IIIa), (IIIb), (IVa) or (IVb).

In a preferred embodiment of the process according to the invention, the substituents of formulae (Ia), (Ib), (II), (IIIa), (IIIb), (IVa), (IVb) are defined as follows:

$R^1$ is $C_1$-$C_6$-alkyl or $C_6$-$C_{14}$-aryl-$C_1$-$C_4$-alkyl,
wherein $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy
$R^2$ and $R^3$ are the same and are selected from $C_1$-$C_4$-alkyl,
$R^4$ is $C_1$-$C_4$-alkyl, $C_1$-$C_4$-haloalkyl, $C_1$-$C_4$-alkoxy, $C_1$-$C_4$-haloalkoxy, phenyl or benzyl,
n is 0, 1 or 2,
each substituent $R^5$, if present, is independently selected from the group consisting of halogen, $C_1$-$C_6$-alkyl and $C_1$-$C_6$-haloalkyl,
$R^6$ is $C_1$-$C_6$-alkyl, $C_1$-$C_6$-haloalkyl, $C_3$-$C_7$-cycloalkyl or $C_6$-$C_{14}$-aryl,
wherein the $C_6$-$C_{14}$-aryl is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl again is unsubstituted or substituted by one to five $C_1$-$C_6$-alkyl substituents,
$R^7$ and $R^8$ are independently from one another hydrogen selected from the group consisting of hydrogen, $C_1$-$C_6$-alkyl, $C_6$-$C_{14}$-aryl, $C_1$-$C_6$-alkoxy or $C_1$-$C_6$-haloalkyl,
wherein the $C_6$-$C_{14}$-aryl is unsubstituted or substituted by one to five $C_1$-$C_4$-alkyl substituents,
$R^9$ and $R^{10}$ are independently from one another selected from the group consisting of $C_1$-$C_6$-alkyl, $C_1$-$C_6$-alkoxy, di($C_1$-$C_6$-alkyl)amino, $C_3$-$C_{12}$-cycloalkyl, $C_6$-$C_{14}$-aryl, $C_6$-$C_{14}$-aryloxy and $C_6$-$C_{14}$-aryl-$C_1$-$C_4$-alkyl,
wherein the $C_1$-$C_6$-alkyl, $C_1$-$C_6$-alkoxy and di($C_1$-$C_6$-alkyl)amino moieties are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and wherein the $C_6$-$C_{14}$-aryl, $C_6$-$C_{14}$-aryloxy and $C_3$-$C_{12}$-cycloalkyl, as such or as part of a composite substituent, in each case is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl is unsubstituted or substituted by one to five $C_1$-$C_6$-alkyl substituents or $R^9$ and $R^{10}$ together with the phosphorus atom to which they are bonded, form a phospholane ring, which may be substituted with one or two $C_1$-$C_6$-alkyl groups, m is 1 or 2, A is

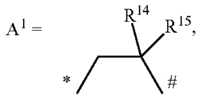

where the bond identified by "*" is bonded directly to the phosphorus atom and where the bond identified by "#" is bonded directly to the oxazoline moiety, $R^{13}$ is $C_3$-$C_6$-alkyl, $C_3$-$C_{12}$-cycloalkyl, $C_6$-$C_{14}$-aryl or $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{14}$ and $R^{15}$ are independently from one another selected from the group consisting of $C_1$-$C_6$-alkyl, $C_3$-$C_{12}$-cycloalkyl, $C_6$-$C_{14}$-aryl and $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{14}$ and $R^{15}$ together with the carbon to which they are bonded, form a $C_5$-$C_6$-cycloalkyl ring, $R^{16}$ and $R^{17}$ are independently from one another selected from the group consisting of $C_1$-$C_6$-alkyl, $C_3$-$C_{12}$-cycloalkyl, $C_6$-$C_{14}$-aryl and $C_6$-$C_{14}$-aryl-$C_1$-$C_4$-alkyl, wherein the $C_1$-$C_6$-alkyl is optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, phenyl, $C_1$-$C_4$-alkoxy, $C_1$-$C_4$-haloalkyl, and $C_1$-$C_4$-haloalkoxy, and wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{16}$ and $R^{17}$ together with the phosphorus atom to which they are bonded, form a phospholane ring, which may be substituted with one or two $C_1$-$C_6$-alkyl groups.

In a more preferred embodiment of the process according to the invention, the substituents of formulae (Ia), (Ib), (II), (IIIa), (IIIb), (IVa), (IVb) are defined as follows:

$R^1$ is $C_1$-$C_6$-alkyl, $R^2$ and $R^3$ are the same and are selected from $C_1$-$C_4$-alkyl, $R^4$ is $C_1$-$C_4$-alkyl, $C_1$-$C_4$-haloalkyl, $C_1$-$C_4$-alkoxy, $C_1$-$C_4$-haloalkoxy, phenyl or benzyl, n is 0, 1 or 2, each substituent $R^5$, if present, is independently selected from the group consisting of halogen, $C_1$-$C_6$-alkyl and $C_1$-$C_6$-haloalkyl, $R^6$ is selected from the group consisting of 1-naphtyl, 2-naphtyl, 9-antracenyl, 9-phenantryl or phenyl, which is unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ and $R^8$ are independently from one another hydrogen or $C_1$-$C_6$-alkyl, $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, and m is 1 or 2, A is

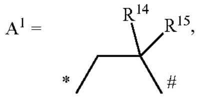

where the bond identified by "*" is bonded directly to the phosphorus atom and where the bond identified by "#" is bonded directly to the oxazoline moiety, $R^{13}$ is selected from the group consisting of $C_3$-$C_6$-alkyl, $C_3$-$C_{12}$-cycloalkyl, $C_6$-$C_{14}$-aryl or $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen or $C_1$-$C_4$-alkyl, $R^{14}$ and $R^{15}$ are independently from one another selected from the group consisting of $C_1$-$C_6$-alkyl and $C_6$-$C_{14}$-aryl-$C_1$-$C_4$-alkyl, wherein the $C_6$-$C_{14}$-aryl in the $C_6$-$C_{14}$-aryl-$C_1$-$C_4$-alkyl moiety is unsubstituted or substituted by one to five substituents selected from the group consisting of halogen and $C_1$-$C_4$-alkyl, $R^{14}$ and $R^{15}$ together with the carbon to which they are bonded, form a $C_5$-$C_6$-cycloalkyl ring, $R^{16}$ and $R^{17}$ are independently from one another selected from the group consisting of $C_1$-$C_6$-alkyl, $C_3$-$C_{12}$-cycloalkyl, $C_6$-$C_{14}$-aryl and $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, phenyl, $C_1$-$C_4$-haloalkyl, $C_1$-$C_4$-alkoxy and $C_1$-$C_4$-haloalkoxy, or $R^{16}$ and $R^{17}$ together with the phosphorus atom to which they are bonded, form a phospholane ring, which may be substituted with one or two $C_1$-$C_6$-alkyl groups.

In the most preferred embodiment of the process according to the invention, the substituents of formulae (Ia), (Ib), (II), (IIIa), (IIIb), (IVa), (IVb) are defined as follows:

$R^1$ is $C_1$-$C_4$-alkyl, $R^2$ and $R^3$ are methyl, $R^4$ is $C_1$-$C_4$-alkyl, n is 0 or 1

$R^5$ if present, is fluorine, $R^6$ phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl 2,4,6-triisopropylphenyl, 9-phenantryl or 2,6-diethyl-4-methylphenyl, $R^7$ is hydrogen, $R^8$ is hydrogen or methyl, $R^9$ and $R^{10}$ are each the same and selected from the group consisting of ethyl, iso-propyl, tert-butyl, cyclopentyl, adamantyl and cyclohexyl, m is 1 or 2, A is

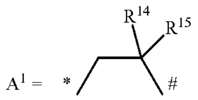

where the bond identified by "*" is bonded directly to the phosphorus atom and where the bond identified by "#" is bonded directly to the oxazoline moiety, $R^{13}$ is tert-butyl, iso-propyl or phenyl, $R^{14}$ and $R^{15}$ are methyl, $R^{16}$ and $R^{17}$ are each the same and 2-methylphenyl or 3,5-bismethylphenyl.

In a preferred embodiment of the process according to the invention, the ligand of the formula (IIIa) or (IIIb) is used. Depending on whether compound (Ia) or (Ib) is the desired product, the ligand of the formula (IIIa) or (IIIb) is selected.

Preferred are ligands of the formulae (IIIa) and (IIIb), wherein the substituents are defined as follows:

$R^6$ is $C_1$-$C_6$-alkyl, $C_1$-$C_6$-haloalkyl, $C_3$-$C_7$-cycloalkyl or $C_6$-$C_{14}$-aryl, wherein the $C_6$-$C_{14}$-aryl is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl again is unsubstituted or substituted by one to five $C_1$-$C_6$-alkyl substituents, $R^7$ and $R^8$ are independently from one another selected from the group consisting of hydrogen, $C_1$-$C_6$-alkyl, $C_1$-$C_6$-alkoxy, $C_6$-$C_{14}$-aryl or $C_1$-$C_6$-haloalkyl, wherein the $C_6$-$C_{14}$-aryl is unsubstituted or substituted by one to five $C_1$-$C_4$-alkyl substituents, $R^9$ and $R^{10}$ are independently from one another selected from the group consisting of $C_1$-$C_6$-alkyl, $C_1$-$C_6$-alkoxy, di($C_1$-$C_6$-alkyl)amino, $C_3$-$C_{12}$-cycloalkyl, $C_6$-$C_{14}$-aryl, $C_6$-$C_{14}$-aryloxy and $C_6$-$C_{14}$-aryl-$C_1$-$C_4$-alkyl, wherein the $C_1$-$C_6$-alkyl, $C_1$-$C_6$-alkoxy and di($C_1$-$C_6$-alkyl)amino moieties are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and wherein the $C_6$-$C_{14}$-aryloxy, $C_3$-$C_{12}$-cycloalkyl and $C_6$-$C_{14}$-aryl, as such or as part of a composite substituent, in each case is unsubstituted or substituted by one to five substituents selected from the group consisting of halogen, $C_1$-$C_4$-alkyl, $C_1$-$C_4$-haloalkyl, $C_1$-$C_4$-alkoxy, $C_1$-$C_4$-haloalkoxy and phenyl, wherein the phenyl is unsubstituted or substituted by one to five $C_1$-$C_6$-alkyl substituents or $R^9$ and $R^{10}$ together with the phosphorus atom to which they are bonded, form a phospholane ring, which may be substituted with one or two $C_1$-$C_6$-alkyl groups, and m is 1 or 2.

More preferred are ligands of the formulae (IIIa) and (IIIb), wherein the substituents are defined as follows:

$R^6$ is selected from the group consisting of 1-naphtyl, 2-naphtyl, 9-antracenyl, 9-phenantryl or phenyl, which is unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ and $R^8$ are independently from one another hydrogen or $C_1$-$C_6$-alkyl, $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, and m is 1 or 2.

Most preferred are ligands of the formulae (IIIa) and (IIIb), wherein the substituents are defined as follows:

$R^6$ is selected from the group consisting of, phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl 2,4,6-triisopropylphenyl, 9-phenantryl or 2,6-diethyl-4-methylphenyl, $R^7$ is hydrogen $R^8$ is hydrogen or methyl, $R^9$ and $R^{10}$ are each the same and tert-butyl, cyclopentyl or cyclohexyl, and m is 1.

In another preferred embodiment of the process according to the invention, the ligand of the formula (IVa) or (IVb) is used. Depending on whether compound (Ia) or (Ib) is the desired product, the ligand of the formula (IVa) or (IVb) is selected.

Preferred are ligands of the formulae (IVa) and (IVb), wherein the substituents are defined as follows:

A is

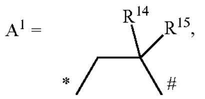

where the bond identified by "*" is bonded directly to the phosphorus atom and where the bond identified by "#" is bonded directly to the oxazoline moiety, $R^{13}$ is $C_3$-$C_6$-alkyl, $C_3$-$C_{12}$-cycloalkyl, $C_6$-$C_{14}$-aryl or $C_6$-$C_{14}$-aryl-$C_1$-$C_4$-alkyl, wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{14}$ and $R^{15}$ are independently from one another selected from the group consisting of $C_1$-$C_6$-alkyl, $C_6$-$C_{14}$-aryl, $C_3$-$C_{12}$-cycloalkyl, and $C_6$-$C_{14}$-aryl-$C_1$-$C_4$-alkyl, wherein $C_6$-$C_{14}$-aryl and the $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^{14}$ and $R^{15}$ together with the carbon to which they are bonded, form a $C_5$-$C_6$-cycloalkyl ring, $R^{16}$ and $R^{17}$ are independently from one another selected from the group consisting of $C_1$-$C_6$-alkyl, $C_3$-$C_{12}$-cycloalkyl, $C_6$-$C_{14}$-aryl and $C_6$-$C_{14}$-aryl-$C_1$-$C_4$-alkyl, wherein the $C_1$-$C_6$-alkyl is optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, phenyl, $C_1$-$C_4$-haloalkyl, $C_1$-$C_4$-alkoxy and $C_1$-$C_4$-haloalkoxy, or $R^{16}$ and $R^{17}$ together with the phosphorus atom to which they are bonded, form a phospholane ring, which may be substituted with one or two $C_1$-$C_6$-alkyl groups.

More preferred are ligands of the formulae (IVa) and (IVb), wherein the substituents are defined as follows:

A is

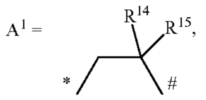

where the bond identified by "*" is bonded directly to the phosphorus atom and where the bond identified by "#" is bonded directly to the oxazoline moiety, $R^{13}$ is iso-propyl, sec-butyl, iso-butyl, tert-butyl, phenyl or benzyl, $R^{14}$ and $R^{15}$ are independently from one another selected from the group consisting of $C_1$-$C_6$-alkyl, and $C_6$-$C_{14}$-aryl-$C_1$-$C_4$-alkyl, wherein the $C_6$-$C_{14}$-aryl in the $C_6$-$C_{14}$-aryl-$C_1$-$C_4$-alkyl moiety is unsubstituted or substituted by one to five substituents selected from the group consisting of halogen and $C_1$-$C_4$-alkyl, $R^{16}$ and $R^{17}$ are independently from one another phenyl, 1-naphthyl or 2-naphthyl, which in each case is unsubstituted or substituted by one to five $C_1$-$C_4$-alkyl substituents Most preferred are ligands of the formulae (IVa) and (IVb), wherein the substituents are defined as follows:

A is

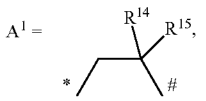

where the bond identified by "*" is bonded directly to the phosphorus atom and where the bond identified by "#" is bonded directly to the oxazoline moiety, $R^{13}$ is tert-butyl, $R^{14}$ and $R^{15}$ are methyl, and $R^{16}$ and $R^{17}$ are independently from one another phenyl, which is substituted by one or two methyl, in particular $R^{16}$ and $R^{17}$ are each the same and phenyl, which is substituted by one or two methyl or $R^{16}$ and $R^{17}$ are each the same and 2-methylphenyl or 3,5-dimethylphenyl.

Preferably, the chiral iridium catalyst is selected from the group consisting of [IrL*(COD)]Y and [IrL*(nbd)]Y, wherein L* is the chiral ligand of the formula (IIIa), (IIIb), (IVa) or (IVb), COD represents 1,5-cyclooctadiene, nbd represents norbornadiene, and Y is a non-coordinating anion selected from the group consisting of $[B(R^{18})_4]^-$, $PF_6^-$, $SbF_6$, $CF_3SO_3^-$, $[Al\{OC(CF_3)_3\}_4]^-$ (VII) and ∆-TRISPHAT (VIII)

(VII)

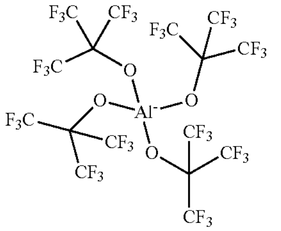

(VIII)

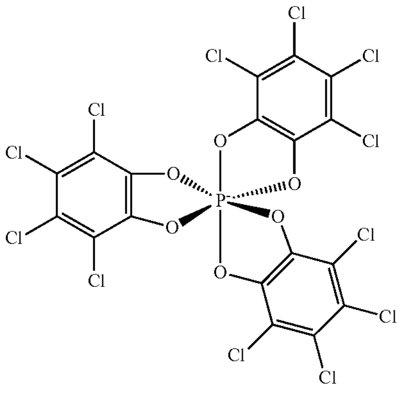

wherein $R^{18}$ is selected from fluorine and phenyl, which is unsubstituted or substituted with one to five substituents selected from $C_1$-$C_4$-alkyl, $C_1$-$C_4$-haloalkyl and halogen.

More preferred are chiral iridium catalysts of the formulae [IrL*(COD)]Y and [IrL*(nbd)]Y, wherein Y is $[Al\{OC(CF_3)_3\}_4]^-$ (VII) or $[B(R^{18})_4]^-$, wherein $R^{18}$ is phenyl, which is unsubstituted or substituted with one to five substituents selected from fluorine and trifluoromethyl.

Even more preferred are chiral iridium catalysts of the general formulae (Va), (Vb), (VIa) and (VIb)

(Va)

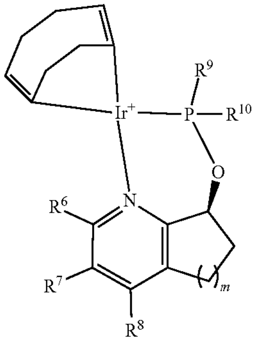

$[B(R^{18})_4]^-$ (Vb)

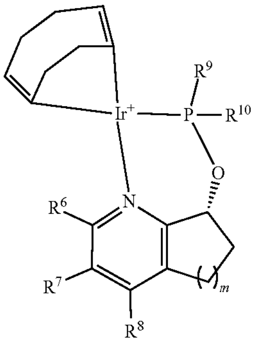

$[B(R^{18})_4]^-$ (VIa)

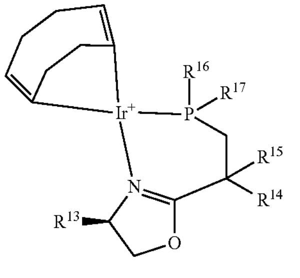

$[B(R^{18})_4]^-$ (VIb)

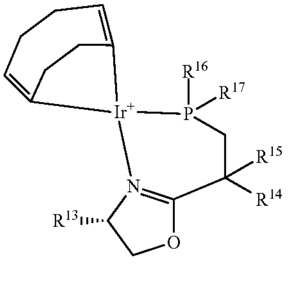

$[B(R^{18})_4]^-$, wherein $R^6$ is selected from the group consisting of 1-naphtyl, 2-naphtyl, 9-antracenyl, 9-phenantryl or phenyl, wherein 1-naphtyl, 2-naphtyl, 9-antracenyl, 9-phenantryl and phenyl are unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ and $R^8$ are independently from one another hydrogen, $C_1$-$C_6$-alkyl or $C_1$-$C_6$-alkoxy $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, m is 1 or 2, $R^{13}$ is iso-propyl, sec-butyl, iso-butyl, tert-butyl, phenyl or benzyl, $R^{14}$ and $R^{15}$ are independently from one another selected from the group consisting of $C_1$-$C_6$-alkyl, and $C_6$-$C_{14}$-aryl-$C_1$-$C_4$-alkyl, wherein the $C_6$-$C_{14}$-aryl in the $C_6$-$C_{14}$-aryl-$C_1$-$C_4$-alkyl moiety is unsubstituted or substituted by one to five substituents selected from the group consisting of halogen and $C_1$-$C_4$-alkyl, $R^{16}$ and $R^{17}$ are independently from one another phenyl, 1-naphthyl or 2-naphthyl, which in each case is unsubstituted or substituted by one to five substituents selected from the group consisting of halogen, $C_1$-$C_4$-alkyl and $C_1$-$C_4$-haloalkyl, and $R^{18}$ is phenyl, which is unsubstituted or substituted with one to five substituents selected from fluorine and $C_1$-$C_4$-haloalkyl.

Particularly preferred are chiral iridium catalysts of the general formulae (Va), (Vb), (VIa) and (VIb), wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl, 2,4,6-triisopropylphenyl, 9-phenantryl and 2,6-diethyl-4-methylphenyl, $R^7$ is hydrogen, $R^8$ is hydrogen or methyl $R^9$ and $R^{10}$ are each the same and tert-butyl, adamantly, cyclopentyl or cyclohexyl, m is 1 or 2, $R^{13}$ is tert-butyl, $R^{14}$ and $R^{15}$ are methyl, $R^{16}$ and $R^{17}$ are independently from one another phenyl, which is substituted by one or two methyl, in particular $R^{16}$ and $R^{17}$ are each the same and 2-methylphenyl or 3,5-dimethylphenyl, and $R^{18}$ is 3,5-bis(trifluoromethyl)phenyl.

In an alternative embodiment the chiral iridium catalysts is of the general formulae (Va) and (Vb), wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl, 2,4,6-triisopropylphenyl, 9-phenantryl and 2,6-diethyl-4-methylphenyl, $R^7$ is hydrogen $R^8$ is $C_1$-$C_6$-alkoxy $R^9$ and $R^{10}$ are independently from one another selected from the group consisting of ethyl, iso-propyl, sec-butyl, iso-butyl, tert-butyl, cyclohexyl, cyclopentyl, adamantyl and benzyl, and m is 1.

The amount of iridium catalyst used is preferably within the range of from 0.001 mol % to 5 mol %, more preferably 0.005 mol % to 4 mol %, most preferably 0.01 mol % to 3 mol %, in particular 0.01 mol % to 2.0 mol %, based on the amount of the compound of the formula (II).

The chiral iridium catalyst may be prepared by methods known in the art from an iridium (I) catalyst precursor, such as $[Ir(COD)Cl]_2$, the chiral ligand of the formula (IIIa), (IIIb), (IVa) or (IVb) and an alkali salt of the non-coordinating anion (S. Kaiser et al., Angew. Chem. Int. Ed. 2006, 45, 5194-5197; W. J. Drury III et al., Angew. Chem. Int. Ed. 2004, 43, 70-74).

The process according to the invention comprises enantioselective hydrogenation of the compound of the formula (II).

Preferably, the hydrogenation is conducted using hydrogen gas at a pressure of from 1 to 300 bar, preferably 3 to 200 bar, most preferably 20 to 150 bar.

The hydrogenation is preferably conducted at a temperature within the range of from 20° C. to 130° C., more preferably 30° C. to 100° C.

Suitable solvents are halogenated alcohols such as 2,2,2,-trifluoroethanol, hexafluoroisopropanol (1,1,1,3,3,3-hexafluoro-2-propanol) and tetrafluoropropanol (2,2,3,3-tetrafluoro-1-propanol), halogenated hydrocarbons, such as chlorobenzene, dichlorobenzene, dichloromethane, chloroform, tetrachloromethane, dichloroethane and trichloroethane, aromatic hydrocarbons such as benzene, toluene and xylene, ethers such as diethyl ether, diisopropyl ether, methyl tert-butyl ether, methyl tert-amyl ether, dioxane, tetrahydrofuran, 1,2-dimethoxyethane, 1,2-diethoxyethane and anisole, and esters such as ethyl acetate, isopropyl acetate, and mixtures thereof.

Preferred solvents are selected from the group consisting of 2,2,2,-trifluoroethanol, hexafluoroisopropanol, 1,2-dichloroethane, tetrafluoropropanol, 1,4-dioxane, isopropyl acetate, toluene, and mixtures thereof.

More preferred solvents are selected from the group consisting of 2,2,2,-trifluoroethanol, hexafluoroisopropanol, 1,2-dichloroethane, tetrafluoropropanol, and mixtures thereof.

Especially preferred are 2,2,2,-trifluoroethanol and hexafluoroisopropanol.

Most preferred is hexafluoroisopropanol.

The hydrogenation may optionally be conducted in presence of an acidic additive, such as acetic acid, trifluoroacetic acid, camphorsulfonic acid, p-toluenesulfonic acid, pivalic acid, benzoic acid, formic acid, butyric acid or oxalic acid. If an acidic additive is used, it is preferably used as a mixture with the solvent.

The amount of acidic used is preferably at most 20 mol %, more preferably at most 10 mol %, and in particular within the range of from 0 to 5 mol %, based on the amount of the compound of the formula (II).

Preparation of Iridium Catalysts

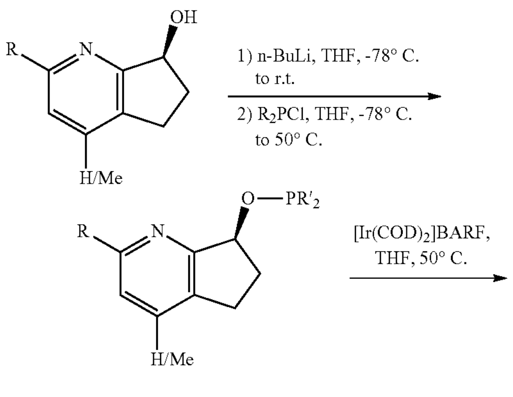

-continued

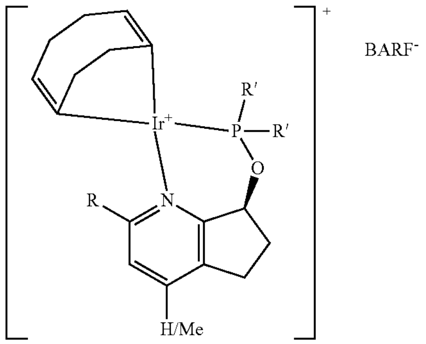

The ligand precursors (enantiomerically enriched secondary alcohols) were prepared according to known literature procedures like to the method disclosed in S. Kaiser et al., Angew. Chem. Int. Ed. 2006, 45, 5194-5197 or in D. H. Woodmansee Chem. Sci 2010, 1, 72. The ligands and Iridium complexes were prepared by a modified procedure based on the same literature precedents:

Procedure of ligand synthesis (under Ar): A solution of alcohol precursor in THF (0.25 mmol, in 5.0 mL THF) was cooled to −78° C. and n-BuLi (0.1 mL of a 2.5 M n-BuLi solution in hexane; 0.25 mmol; 1 eq.) was added dropwise to the continuously stirred solution. After completion of the addition the solution was allowed to warm to room temperature and was stirred at this temperature for further 30 min. The solution was cooled to −78° C. again and $R_2PCl$ (0.25 mmol, 1 eq.) was added to the continuously stirred solution. The mixture was allowed to warm to room temperature and subsequently heated to 50° C. and kept at this temperature overnight. The theoretical yield of ligand was calculated using $^{31}P$-NMR and the ligand was used for the next step without further purification.

Procedure of complexation (under Ar): To the crude ligand solution was added $[Ir(COD)_2]BARF$ (BARF= Tetrakis[3,5-bis(trifluoromethyl)phenyl]-borate) (as a solid, 1 eq. based on the theoretical yield). The resulting mixture was heated to 50° C. and kept at this temperature for 3 h.

Work-up (under air): After cooling to room temperature the reaction solution is rotary evaporated onto silica, loaded onto a column of silica. Side components were eluted using pentane/diethylether and the desired complexes subsequently with DCM. The solvent was then evaporated under reduced pressure.

The following specified catalysts were synthesized and characterized:

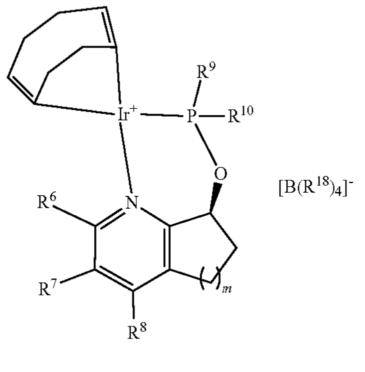

with m=1 and $R^{18}$=3,5-bis(trifluoromethyl)phenyl

| Catalyst | $R^6$ | $R^7$ | $R^8$ | $R^9$, $R^{10}$ |
|---|---|---|---|---|
| Va-1 | phenyl | H | H | tert-butyl |
| Va-2 | phenyl | H | methyl | tert-butyl |
| Vb-3 | phenyl | H | H | cyclohexyl |
| Va-4 | phenyl | H | methyl | cyclohexyl |
| Vb-5 | 4-tert-butylphenyl | H | H | cyclohexyl |
| Va-6 | 4-tert-butylphenyl | H | methyl | cyclohexyl |
| Vb-7 | 9-antracenyl | H | H | cyclohexyl |
| Va-8 | 9-antracenyl | H | methyl | cyclohexyl |
| Va-9 | 2,6-dimethylphenyl | H | methyl | cyclohexyl |
| Va-10 | 2,4,6-trimethylphenyl | H | methyl | cyclohexyl |
| Va-11 | 3,5-dimethylphenyl | H | methyl | cyclohexyl |
| Va-12 | 1-naphtyl | H | methyl | cyclohexyl |
| Va-13 | 4-methoxyphenyl | H | methyl | tert-butyl |
| Va-14 | 4-fluorophenyl | H | methyl | tert-butyl |
| Va-15 | 4-(trifluoromethyl)phenyl | H | methyl | tert-butyl |
| Va-16 | phenyl | H | methyl | cyclopentyl |
| Vb-17 | phenyl | H | H | ethyl |
| Va-18 | phenyl | H | methyl | isopropyl |
| Va-19 | methyl | H | methyl | cyclohexyl |
| Va-20 | 3,5-bis-tert.-butyl,-4-methoxyphenyl | H | methyl | cyclohexyl |
| Va-21 | 2,4,6-triisopropylphenyl | H | methyl | cyclohexyl |
| Va-22 | 4-tert-butyl-2,6-dimethylphenyl | H | methyl | cyclohexyl |
| Va-23 | phenyl | H | H | adamantyl |

Va-2

The reaction was performed according to the above described procedure. The complex could be isolated as an orange solid (89.5 mg; 53% based on $[Ir(COD)_2]$BARF).

$^1$H-NMR (300 MHz, $CD_2Cl_2$): δ (ppm)=8.26 (dd, J=7.9, 1.7 Hz, 2H), 7.81-7.36 (m, 16H), 5.75 (dt, J=8.0, 5.2 Hz, 1H), 5.34-5.29 (m, 1H), 4.51 (q, J=5.3, 3.2 Hz, 1H), 4.11 (dq, J=12.5, 7.6, 5.9 Hz, 1H), 3.08 (ddd, J=16.6, 10.3, 3.8 Hz, 1H), 2.99-2.70 (m, 2H), 2.61-2.00 (m, 8H), 1.92-1.79 (m, 1H), 1.69 (dd, J=14.8, 8.1 Hz, 1H), 1.51 (s, 9H), 1.29-1.24 (m, 3H), 1.06 (d, J=14.4 Hz, 9H). $^{31}$P-NMR (122 MHz, $CD_2Cl_2$) δ (ppm)=142.09. $^{19}$F-NMR (282 MHz, $CD_2Cl_2$) δ (ppm)=−62.85. HR-MS (ESI) m/z calcd for $C_{31}H_{44}$NOPIr [M]+670.2790 found 670.2798.

Va-4

The reaction was performed according to the above described procedure. The complex could be isolated as an orange solid (241 mg; 71% based on $[Ir(COD)_2]$BARF).

$^1$H-NMR (300 MHz, $CD_2Cl_2$): δ (ppm)=8.38-8.14 (m, 2H), 7.83-7.43 (m, 16H), 5.76 (dt, J=7.7, 4.9 Hz, 1H), 4.81 (t, J=7.6 Hz, 1H), 4.70-4.46 (m, 1H), 3.56-3.39 (m, 1H), 3.06 (ddd, J=16.7, 10.3, 3.6 Hz, 1H), 2.98-2.73 (m, 2H), 2.71-2.57 (m, 1H), 2.44 (s, 3H), 2.41-2.02 (m, 6H), 2.00-1.75 (m, 7H), 1.72-1.54 (m, 4H), 1.46-0.94 (m, 13H), 0.72-0.50 (m, 1H). $^{31}$P-NMR (122 MHz, $CD_2Cl_2$) δ (ppm) =121.27. $^{19}$F-NMR (282 MHz, $CD_2Cl_2$) δ (ppm)=−62.86. HR-MS (ESI) m/z calcd for $C_{35}H_{48}$NOPIr [M]+722.3103 found 722.3116.

Vb-5

The reaction was performed according to the above described procedure using 287 mg of $[Ir(COD)_2]$BARF (0.225 mmol). The complex could be isolated as an orange solid (261 mg; 74% based on $[Ir(COD)_2]$BARF).

$^1$H-NMR (300 MHz, $CD_2Cl_2$): δ (ppm)=8.25 (d, J=8.3 Hz, 2H), 7.87 (d, J=8.1 Hz, 1H), 7.81-7.64 (m, 11H), 7.56 (s, 4H), 5.74 (dt, J=8.2, 4.6 Hz, 1H), 4.95-4.74 (m, 1H), 4.74-4.51 (m, 1H), 3.60-3.45 (m, 1H), 3.23-2.91 (m, 2H), 2.90-2.70 (m, 1H), 2.67-2.50 (m, 1H), 2.52-2.23 (m, 4H), 2.28-2.04 (m, 3H), 2.04-1.77 (m, 7H), 1.69-1.58 (m, 4H), 1.45-1.26 (m, 17H), 1.17-0.95 (m, 4H), 0.68-0.42 (m, 1H). $^{31}$P-NMR (122 MHz, $CD_2Cl_2$) δ (ppm)=121.12. $^{19}$F-NMR (282 MHz, $CD_2Cl_2$) δ (ppm)=−62.85. HR-MS (ESI) m/z calcd for $C_{38}H_{54}$NOPIr [M]+764.3572 found 764.3586.

Va-6

The reaction was performed according to the above described procedure. The complex could be isolated as an orange solid (286 mg; 64% based on $[Ir(COD)_2]$BARF).

$^1$H-NMR (300 MHz, $CDCl_3$): δ (ppm)=8.20 (d, J=8.2 Hz, 2H), 7.77-7.69 (m, 8H), 7.66 (d, J=8.4 Hz, 2H), 7.53 (d, J=4.9 Hz, 5H), 5.77-5.67 (m, 1H), 4.78 (d, J=7.6 Hz, 1H), 4.57 (s, 1H), 3.47 (s, 1H), 3.08-2.89 (m, 1H), 2.89-2.66 (m, 2H), 2.59 (p, J=7.4 Hz, 1H), 2.47-1.74 (m, 15H), 1.42 (s, 17H), 1.18-0.78 (m, 5H), 0.72-0.48 (m, 1H). $^{31}$P-NMR (122 MHz, $CDCl_3$) 121.31. $^{19}$F-NMR (282 MHz, $CDCl_3$) δ=−62.42. HR-MS (ESI): m/z calculated for $[C_{39}H_{56}$NOP193Ir]+:778.3729 found 778.3732.

Vb-7

The reaction was performed according to the above described procedure using 287 mg of $[Ir(COD)_2]$BARF (0.225 mmol). The complex could be isolated after two time purification as an orange solid (151 mg; 36% based on $[Ir(COD)_2]$BARF).

$^1$H-NMR (300 MHz, $CD_2Cl_2$): δ (ppm)=8.84 (s, 1H), 8.38-8.27 (m, 1H), 8.21 (ddt, J=8.5, 1.3, 0.7 Hz, 1H), 8.18-8.02 (m, 2H), 7.83-7.72 (m, 10H), 7.72-7.54 (m, 6H), 7.49 (ddd, J=8.8, 6.6, 1.4 Hz, 1H), 7.23-6.96 (m, 1H), 5.74-5.54 (m, 1H), 5.26-5.12 (m, 1H), 4.41-4.18 (m, 1H), 3.53-3.15 (m, 3H), 2.75-2.61 (m, 2H), 2.59-2.32 (m, 2H), 2.18-1.91 (m, 6H), 1.92-1.74 (m, 5H), 1.74-1.56 (m, 2H), 1.48-1.21 (m, 10H), 1.18-0.99 (m, 1H), 0.96-0.59 (m, 2H), 0.39-0.15 (m, 1H), 0.06--0.11 (m, 1H). $^{31}$P-NMR (122 MHz, $CD_2Cl_2$) δ (ppm)=120.30. $^{19}$F-NMR (282 MHz, $CD_2Cl_2$) δ (ppm)=−62.87. HR-MS (ESI) m/z calcd for $C_{42}H_{50}$NOPIr [M]+808.3259 found 808.3278.

Va-8

The reaction was performed according to the above described procedure using 287 mg of $[Ir(COD)_2]$BARF (0.225 mmol). The complex could be isolated using DCM (100%) to afford an orange solid (296 mg; 78% based on $[Ir(COD)_2]$BARF).

$^1$H-NMR (300 MHz, $CD_2Cl_2$): δ (ppm)=8.68 (s, 1H), 8.23-7.85 (m, 3H), 7.75-7.23 (m, 17H), 7.05 (dq, J=8.8, 1.0 Hz, 1H), 5.61-5.40 (m, 2H), 5.12-4.88 (m, 1H), 4.24-4.00 (m, 1H), 3.25-2.88 (m, 3H), 2.58-2.46 (m, 2H), 2.44-2.14 (m, 7H), 2.08-1.61 (m, 11H), 1.61-1.37 (m, 5H), 1.37-1.07 (m, 6H), 1.03-0.85 (m, 1H), 0.65-0.45 (m, 1H), 0.16 (dtd, J=15.8, 10.4, 5.6 Hz, 1H), −0.16 (dt, J=13.2, 9.1 Hz, 1H). $^{31}$P-NMR (122 MHz, CD2Cl2) δ=120.57. $^{19}$F-NMR (282 MHz, CD2Cl2) δ=−62.86. HR-MS (ESI) m/z calcd for $C_{43}H_{52}$NOPIr [M]+822.3416 found 822.3416.

Va-9

The reaction was performed according to the above described procedure using 287 mg of $[Ir(COD)_2]$BARF (0.225 mmol). The complex could be isolated as an orange solid (298 mg; 82% based on $[Ir(COD)_2]$BARF).

$^1$H-NMR (300 MHz, $CD_2Cl_2$): δ (ppm)=7.80-7.52 (m, 12H), 7.42-7.19 (m, 3H), 7.12 (d, J=7.5 Hz, 1H), 5.65 (td, J=5.6, 2.6 Hz, 1H), 5.48-5.42 (m, 1H), 4.43-4.37 (m, 1H), 3.38-3.30 (m, 1H), 3.21-2.89 (m, 3H), 2.67 (s, 3H), 2.58-2.45 (m, 2H), 2.42 (s, 3H), 2.38-2.16 (m, 2H), 2.13-2.05 (m, 3H), 2.02-1.89 (m, 4H), 1.84 (s, 3H), 1.81-1.72 (m, 2H), 1.64-1.49 (m, 3H), 1.39-1.19 (m, 8H), 1.12-0.99 (m, 4H), 0.68-0.56 (m, 1H). $^{31}$P-NMR (122 MHz, $CD_2Cl_2$) δ=118.80. $^{19}$F-NMR (282 MHz, $CD_2Cl_2$) δ=−62.88. HR-MS (ESI) m/z calcd for $C_{37}H_{52}$NOPIr [M]+750.3416 found 750.3420.

Va-10

The reaction was performed according to the above described procedure using 287 mg of $[Ir(COD)_2]$BARF (0.225 mmol). The complex could be isolated as an orange solid (148 mg; 40% based on $[Ir(COD)_2]BARF$).

$^1$H-NMR (300 MHz, $CD_2Cl_2$): δ (ppm)=7.91-7.46 (m, 12H), 7.21 (s, 1H), 7.09 (s, 1H), 6.94 (s, 1H), 5.67-5.63 (m, 1H), 5.46-5.41 (m, 1H), 4.38-4.36 (m, 1H), 3.36-3.32 (m, 1H), 3.19-2.85 (m, 3H), 2.64 (s, 3H), 2.53-2.46 (m, 2H), 2.41 (s, 3H), 2.35 (s, 3H), 2.31-2.18 (m, 2H), 2.19-1.83 (m, 14H), 1.68-1.54 (m, 6H), 1.38-1.20 (m, 5H), 1.14-0.97 (m, 5H), 0.68-0.56 (m, 1H). $^{31}$P-NMR (122 MHz, $CD_2Cl_2$) δ=118.64. $^{19}$F-NMR (282 MHz, $CD_2Cl_2$) δ=−62.87. HR-MS (ESI) m/z calcd for $C_{38}H_{54}NOPIr$ [M]+764.3572 found 764.3577.

Va-11

The reaction was performed according to the above described procedure using 287 mg of $[Ir(COD)_2]BARF$ (0.225 mmol). The complex could be isolated using DCM (100%) to afford an orange solid (310 mg; 85% based on $[Ir(COD)_2]BARF$).

$^1$H-NMR (300 MHz, $CD_2Cl_2$): δ (ppm)=7.86 (s, 2H), 7.79-7.47 (m, 13H), 7.36 (s, 1H), 5.79-5.62 (m, 1H), 4.78-4.74 (m, 1H), 4.57-4.53 (m, 1H), 3.56-3.48 (m, 1H), 3.13-2.95 (m, 1H), 2.95-2.61 (m, 3H), 2.51 (s, 6H), 2.47-2.36 (m, 5H), 2.34-2.03 (m, 5H), 2.03-1.77 (m, 7H), 1.71-1.47 (m, 7H), 1.45-1.19 (m, 5H), 1.19-0.98 (m, 4H), 0.70-0.62 (m, 1H). $^{31}$P-NMR (122 MHz, $CD_2Cl_2$) δ=121.65. $^{19}$F-NMR (282 MHz, $CD_2Cl_2$) δ=−62.88. HR-MS (ESI) m/z calcd for $C_{37}H_{52}NOPIr$ [M]+750.3416 found 750.3406.

Va-12

The reaction was performed according to the above described procedure using 287 mg of $[Ir(COD)_2]BARF$ (0.225 mmol). The complex could be isolated as an orange solid (286 mg; 78% based on $[Ir(COD)_2]BARF$).

$^1$H-NMR (300 MHz, $CD_2Cl_2$): δ (ppm)=8.61-8.48 (m, 1H), 8.28-8.15 (m, 1H), 8.11-7.98 (m, 1H), 7.98-7.81 (m, 1H), 7.79-7.50 (m, 16H), 5.70 (ddd, J=8.1, 4.9, 3.2 Hz, 1H), 5.37-5.25 (m, 1H), 4.79 (d, J=10.4 Hz, 1H), 3.53-3.41 (m, 1H), 3.13 (ddd, J=17.2, 9.5, 4.9 Hz, 1H), 2.96 (ddd, J=17.1, 9.4, 4.9 Hz, 1H), 2.88-2.66 (m, 1H), 2.49-2.34 (m, 7H), 2.27-2.14 (m, 1H), 2.09-1.56 (m, 15H), 1.43-1.12 (m, 9H), 1.06-0.92 (m, 1H), 0.78-0.59 (m, 1H), 0.42-0.25 (m, 1H). $^{31}$P-NMR (122 MHz, $CD_2Cl_2$) δ=121.69. $^{19}$F-NMR (282 MHz, $CD_2Cl_2$) δ=−62.87. HR-MS (ESI) m/z calcd for $C_{39}H_{50}NOPIr$ [M]+722.3259 found 722.3262.

Va-13

The reaction was performed according to the above described procedure. The theoretical yield of the ligand was 51%. The complex could be isolated as an orange solid (78.0 mg; 39% based on $[Ir(COD)_2]BARF$).

$^1$H-NMR (300 MHz, $CDCl_3$): δ (ppm)=8.22 (d, J=8.7 Hz, 2H), 7.80-7.63 (m, 8H), 7.63-7.43 (m, 5H), 7.16 (d, J=8.8 Hz, 2H), 5.82-5.66 (m, 1H), 5.37-5.22 (m, 1H), 4.56-4.41 (m, 1H), 4.18-4.00 (m, 1H), 3.93 (s, 3H), 3.12-2.97 (m, 1H), 2.96-2.74 (m, 2H), 2.70-2.56 (m, 1H), 2.43 (s, 3H), 2.41-2.03 (m, 4H), 1.96-1.84 (m, 1H), 1.72 (dd, J=14.6, 7.9 Hz, 1H), 1.51 (d, J=15.0 Hz, 9H), 1.34-1.23 (m, 3H), 1.05 (d, J=14.4 Hz, 9H). $^{31}$P-NMR (122 MHz, $CD_2Cl_2$) δ (ppm)=141.86. $^{19}$F-NMR (282 MHz, $CD_2Cl_2$) δ (ppm)=−62.85. HR-MS (ESI) m/z calcd for $C_{32}H_{46}NO_2PIr$ [M]+700.2895 found 700.2899.

Va-14

The reaction was performed according to the above described procedure using 287 mg of $[Ir(COD)_2]BARF$ (0.225 mmol). The complex could be isolated as an orange solid (245 mg; 70% based on $[Ir(COD)_2]BARF$).

$^1$H-NMR (300 MHz, $CDCl_3$): δ (ppm)=8.38-8.12 (m, 2H), 7.82-7.63 (m, 8H), 7.51 (s, 5H), 7.44-7.17 (m, 2H), 5.81-5.63 (m, 1H), 4.81-4.67 (m, 1H), 4.67-4.49 (m, 1H), 3.57-3.35 (m, 1H), 3.05-2.90 (m, 1H), 2.88-2.61 (m, 3H), 2.36 (s, 3H), 2.31-2.04 (m, 7H), 2.01-1.73 (m, 7H), 1.70-1.48 (m, 6H), 1.42-1.20 (m, 6H), 1.16-0.97 (m, 4H), 0.63-0.40 (m, 1H). $^{31}$P-NMR (122 MHz, $CDCl_3$) δ (ppm)=121.31. $^{19}$F-NMR (282 MHz, $CDCl_3$) δ (ppm)=−62.43, −106.61. HR-MS (ESI) m/z calcd for $C_{35}H_{47}NOFPIr$ [M]+740.3009 found 740.3013.

Va-15

The reaction was performed according to the above described procedure using 287 mg of $[Ir(COD)_2]BARF$ (0.225 mmol). The complex could be isolated as an orange solid (180.0 mg; 48% based on $[Ir(COD)_2]BARF$).

$^1$H-NMR (300 MHz, $CD_2Cl_2$): δ (ppm)=8.46 (d, J=7.9 Hz, 2H), 7.94 (d, J=8.0 Hz, 2H), 7.82-7.38 (m, 13H), 5.83-5.69 (m, 1H), 4.94-4.78 (m, 1H), 4.73-4.54 (m, 1H), 3.65-3.38 (m, 1H), 3.15-2.72 (m, 3H), 2.61-2.27 (m, 7H), 2.25-2.04 (m, 4H), 2.04-1.72 (m, 8H), 1.75-1.58 (m, 3H), 1.43-1.22 (m, 8H), 1.19-0.93 (m, 1H), 0.63-0.44 (m, 1H). $^{31}$P-NMR (122 MHz, $CD_2Cl_2$) δ (ppm)=121.74. $^{19}$F-NMR (282 MHz, $CD_2Cl_2$) δ (ppm)=−62.88, −63.40. HR-MS (ESI) m/z calcd for $C_{36}H_{47}NOF_3PIr$ [M]+790.2977 found 790.2990.

Va-16

The reaction was performed according to the above described procedure. The theoretical yield of the ligand was 90%. The complex could be isolated as an orange solid (261 mg; 75% based on $[Ir(COD)_2]BARF$).

$^1$H-NMR (300 MHz, $CD_2Cl_2$): δ (ppm)=8.28-8.11 (m, 2H), 7.93-7.45 (m, 16H), 5.81 (dt, J=9.3, 5.0 Hz, 1H), 4.89 (t, J=6.9 Hz, 1H), 4.72-4.51 (m, 1H), 3.86-3.66 (m, 1H), 3.18-3.04 (m, 1H), 3.04-2.57 (m, 4H), 2.49 (s, 3H), 2.46-1.61 (m, 18H), 1.56-1.36 (m, 5H), 1.36-1.14 (m, 1H), 1.13-0.93 (m, 1H), 0.77-0.66 (m, 1H). $^{31}$P-NMR (122 MHz, $CD_2Cl_2$) δ (ppm)=129.37. $^{19}$F-NMR (282 MHz, $CD_2Cl_2$) δ (ppm)=−62.88. HR-MS (ESI) m/z calcd for $C_{33}H_{44}NOPIr$ [M]+694.2790 found 694.2789.

Vb-17

The reaction was performed according to the above described procedure. The complex could be isolated as an orange solid (134 mg; 95% purity based on 31P-NMR; 39% based on $[Ir(COD)_2]BARF$).

$^1$H-NMR (300 MHz, $CDCl_3$): δ (ppm) 8.00-7.92 (m, 2H), 7.81-7.76 (m, 1H), 7.75-7.64 (m, 10H), 7.62-7.55 (m, 2H), 7.52 (d, J=1.9 Hz, 4H), 5.88 (dt, J=8.3, 4.9 Hz, 1H), 4.52 (dt, J=8.3, 4.2 Hz, 1H), 4.37 (ddt, J=7.4, 5.0, 2.5 Hz, 1H), 3.61 (td, J=8.0, 3.8 Hz, 1H), 3.17-2.64 (m, 4H), 2.34-1.79 (m, 9H), 1.68-1.55 (m, 1H), 1.36-0.90 (m, 9H). $^{31}$P-NMR (122 MHz, $CDCl_3$) δ=116.36 (mayor product: 95%), 111.79 (minor species; 5%). $^{19}$F-NMR (282 MHz, $CDCl_3$) δ=−62.41. HR-MS (ESI) m/z calcd for $C_{26}H_{34}NOPIr$ [M]+600.2006 found 600.2006.

Va-18

The reaction was performed (0.5 mmol scale) according to the above described procedure, but after the addition of $ClP(iPr)_2$ was completed, the reaction mixture was stirred at RT for 16 h. The complex could be isolated as an orange solid (605 mg; 85% based on $[Ir(COD)_2]BARF$).

$^1$H-NMR (300 MHz, $CDCl_3$): δ (ppm)=8.17 (dd, J=7.1, 1.8 Hz, 2H), 7.78-7.40 (m, 16H), 5.74 (dt, J=9.0, 4.7 Hz, 1H), 4.83 (t, J=6.9 Hz, 1H), 4.61 (dt, J=8.7, 4.1 Hz, 1H), 3.62-3.53 (m, 1H), 3.11-2.94 (m, 1H), 2.91-2.67 (m, 2H), 2.67-2.44 (m, 2H), 2.39 (s, 3H), 2.36-1.93 (m, 6H), 1.85 (dd, J=14.5, 7.3 Hz, 1H), 1.46 (dd, J=15.2, 7.1 Hz, 3H), 1.39-1.31 (m, 1H), 1.23 (dd, J=13.3, 6.9 Hz, 4H), 1.08 (dd, J=19.4, 7.1 Hz, 3H), 0.52 (dd, J=15.5, 7.1 Hz, 3H). $^{31}$P-NMR (122 MHz, $CDCl_3$) δ (ppm)=129.53. $^{19}$F-NMR (282

MHz, $CDCl_3$) δ (ppm)=−62.42. HR-MS (ESI) m/z calcd for $C_{29}H_{40}NOPIr$ [M]+642.2477 found 642.2480.

Va-19

The reaction was performed according to the above described procedure. The complex could be isolated as an orange solid (249 mg; 73% based on $[Ir(COD)_2]BARF$).

$^1H$-NMR (300 MHz, $CD_2Cl_2$): δ (ppm)=7.81-7.61 (m, 9H), 7.56 (d, J=2.0 Hz, 4H), 7.34 (d, J=8.0 Hz, 1H), 5.76 (dt, J=8.7, 4.5 Hz, 1H), 5.05-4.84 (m, 2H), 3.74-3.57 (m, 1H), 3.56-3.36 (m, 1H), 3.07 (s, 3H), 3.01-1.49 (m, 23H), 1.42-1.01 (m, 9H), 0.85-0.70 (m, 1H), 0.51-0.25 (m, 1H). $^{31}P$-NMR (122 MHz, $CD_2Cl_2$) δ (ppm)=126.20. $^{19}F$-NMR (282 MHz, $CD_2Cl_2$) δ (ppm)=−62.88. HR-MS (ESI) m/z calcd for $C_{29}H_{44}NOPIr$ [M]+644.2766 found 644.2762.

Va-20

The reaction was performed according to the above described procedure. The complex could be isolated as an orange solid (164 mg; 42% based on $[Ir(COD)_2]BARF$).

$^1H$-NMR (300 MHz, $CD_2Cl_2$): δ (ppm)=7.86-7.62 (m, 10H), 7.56 (s, 4H), 7.38 (s, 1H), 5.72 (dt, J=8.1, 5.2 Hz, 1H), 4.85-4.63 (m, 2H), 3.80 (s, 3H), 3.49-3.30 (m, 1H), 3.18-2.60 (m, 4H), 2.54-2.23 (m, 6H), 2.23-1.57 (m, 16H), 1.53-1.49 (m, 20H), 1.46-0.93 (m, 10H). $^{31}P$-NMR (122 MHz, $CD_2Cl_2$) δ (ppm)=123.26. $^{19}F$-NMR (282 MHz, $CD_2Cl_2$) δ (ppm)=−62.87. HR-MS (ESI) m/z calcd for $C_{44}H_{66}NO_2PIr$ [M]+864.4460 found 864.4448.

Va-21

The reaction was performed according to the above described procedure. The complex could be isolated as an orange solid (51 mg; 14% based on $[Ir(COD)_2]BARF$).

$^1H$-NMR (400 MHz, $CD_2Cl_2$): δ (ppm)=7.80-7.64 (m, 8H), 7.56 (s, 4H), 7.23 (s, 2H), 7.04 (s, 1H), 5.65 (dt, J=5.9, 3.7 Hz, 1H), 5.45-5.35 (m, 1H), 4.04 (ddd, J=8.2, 5.4, 3.6 Hz, 1H), 3.34 (dd, J=11.2, 6.4 Hz, 1H), 3.19-3.08 (m, 3H), 3.06-2.89 (m, 2H), 2.56-2.44 (m, 2H), 2.41 (s, 3H), 2.33-1.84 (m, 9H), 1.84-1.43 (m, 15H), 1.35-1.24 (m, 12H), 1.23-1.14 (m, 5H), 1.09 (dd, J=10.0, 6.8 Hz, 6H), 0.95 (d, J=6.6 Hz, 3H), 0.60-0.46 (m, 1H). $^{31}P$-NMR (162 MHz, $CD_2Cl_2$) δ (ppm)=119.43. $^{19}F$-NMR (282 MHz, $CD_2Cl_2$) δ (ppm)=−62.86. HR-MS (ESI) m/z calcd for $C_{44}H_{66}NOPIr$ [M]+848.4511 found 848.4512.

Va-22

The reaction was performed according to the above described procedure. The complex could be isolated as an orange solid (274 mg; 73% based on $[Ir(COD)_2]BARF$).

$^1H$-NMR (300 MHz, $CD_2Cl_2$): 8 (ppm)=7.79-7.66 (m, 8H), 7.56 (s, 4H), 7.29 (s, 1H), 7.23 (s, 1H), 7.13 (s, 1H), 5.65 (td, J=5.9, 2.2 Hz, 1H), 5.46-5.40 (m, 1H), 4.42-4.36 (m, 1H), 3.38-3.30 (m, 1H), 3.19-2.86 (m, 3H), 2.65 (s, 3H), 2.59-2.44 (m, 2H), 2.42 (s, 3H), 2.38-1.54 (m, 20H), 1.46-0.98 (m, 21H), 0.70-0.58 (m, 1H). $^{31}P$-NMR (122 MHz, $CD_2Cl_2$) δ (ppm)=118.67. $^{19}F$-NMR (282 MHz, $CD_2Cl_2$) δ (ppm)=−62.86. HR-MS (ESI) m/z calcd for $C_{41}H_{60}NOPIr$ [M]+806.4042 found 806.4053.

Va-23

The reaction was performed according to the above described procedure. The complex could be isolated as an orange solid (15.6 mg; 20% based on $[Ir(COD)_2]BARF$).

$^1H$-NMR (300 MHz, $CD_2Cl_2$) δ=8.43-8.36 (m, 2H), 7.92-7.85 (m, 1H), 7.81-7.69 (m, 12H), 7.68-7.53 (m, 4H), 5.73-5.65 (m, 1H), 5.50-5.43 (m, 1H), 4.58-4.43 (m, 2H), 3.25-3.12 (m, 1H), 3.08-2.94 (m, 1H), 2.92-2.77 (m, 1H), 2.72-1.45 (m, 40H). $^{19}F$-NMR (282 MHz, $CDCl_3$) δ=−62.42. $^{31}P$-NMR (122 MHz, $CD_2Cl_2$) δ=134.32. HR-MS (TOF) m/z calcd for $C_{42}H_{54}NOPIr$ [M]+812.3572 found 812.3578.

EXAMPLES

Reactions were performed in metal autoclaves. Reaction mixtures were analyzed without workup via HPLC (Chiralpak IC column, 95/5 heptane/ethanol, 1 mL/min) or SFC (OZ-H column, 2.5% MeOH in supercritical $CO_2$, 3 mL/min) chromatography.

Example 1

A 600 mL autoclave was filled with 21 g of 1-(2,2,4-trimethyl-1-quinolyl) ethanone (97.5 mmol, 1 equiv), 0.74 g of catalyst (Va-1) (0.48 mmol, 0.5 mol %) and 450 mL of 2,2,2-trifluoroethanol. The autoclave was pressurized with argon three times, followed by pressurization with hydrogen twice. Subsequently, the autoclave was pressurized with 60 bar of hydrogen, heated to 85° C. and the reaction mixture was stirred at that temperature for 72 h. Chromatographic analysis of the cooled and de-pressurized reaction mixture showed complete conversion of starting material to the hydrogenated product 1-[2,2,4-trimethyl-3,4-dihydroquinolin-1-yl]ethanone (97% a/a purity according to SFC analysis) with an enantioselectivity of >98% ee.

Example 2

A 16 mL autoclave was filled with 0.7 g of 1-(2,2,4-trimethyl-1-quinolyl) ethanone (3.3 mmol, 1 equiv), 4.9 mg of catalyst (Va-1) (3.3 μmol, 0.1 mol %) and 4.2 mL of 1,1,1,3,3,3-hexafluor-2-propanol. The autoclave was pressurized with argon three times, followed by pressurization with hydrogen twice. Subsequently, the autoclave was pressurized with 60 bar of hydrogen, heated to 85° C. and the reaction mixture was stirred at that temperature for 16 h. Chromatographic analysis of the cooled and de-pressurized reaction mixture showed 99.3% a/a HPLC conversion of starting material to the hydrogenated product 1-[2,2,4-trimethyl-3,4-dihydroquinolin-1-yl]ethanone with an enantioselectivity of 97.5% ee.

$^1H$-NMR (400 MHz, $CDCl_3$) δ (ppm)=7.12-7.21 (m, 3H), 6.90-6.97 (m, 1H), 2.7-2.83 (m, 1H), 2.09 (s, 3H), 1.83 (d, 1H), 1.72 (s, 3H), 1.49 (s, 3H), 1.35 (d, 2H), 1.22 (t, 1H). UPLC-MS: $R_t$: 1.26 min, UV (210 nm): 100%, m/z (ES+) 218.3. GC-MS: $R_t$: 4.78 min, m/z (RInt, %): 217 (15), 202 (10), 175 (5), 160 (100).

Example 3

A 16 mL autoclave was filled with 0.52 g of 1-(2,2,4-trimethyl-1-quinolyl) ethanone (2.41 mmol, 1 equiv), 9.2 mg of catalyst (Va-1) (6 μmol, 0.25 mol %) and 6 mL of 1,1,1,3,3,3-hexafluoro-2-propanol. The autoclave was pressurized with argon three times, followed by pressurization with hydrogen twice. Subsequently, the autoclave was pressurized with 60 bar of hydrogen, heated to 85° C. and the reaction mixture was stirred at that temperature for 15 h. Chromatographic analysis of the cooled and de-pressurized reaction mixture showed 99.8% a/a HPLC conversion of starting material to the hydrogenated product 1-[2,2,4-trimethyl-3,4-dihydroquinolin-1-yl]ethanone with an enantioselectivity of 96.5% ee.

Example 4

A 100 mL autoclave was filled with 5 g of 1-(6-fluoro-2,2,4-trimethyl-1-quinolyl) ethanone (21.4 mmol, 1 equiv), 65 mg of catalyst (Va-1) (40 μmol, 0.2 mol %) and 50 mL of 1,1,1,3,3,3-hexafluoro-2-propanol. The autoclave was pressurized with argon three times, followed by pressurization with hydrogen twice. Subsequently, the autoclave was pressurized with 60 bar of hydrogen, heated to 85° C. and the reaction mixture was stirred at that temperature for 36 h. From the cooled and de-pressurized reaction mixture the solvent was evaporated to dryness under reduced pressure giving 5.6 g of the hydrogenated product 1-(6-fluoro-2,2,4-trimethyl-3,4-dihydroquinolin-1-yl) ethanone (88.9% w/w purity, 98.7% yield) with an enantioselectivity of 98% ee.

Example 5

A 16 mL autoclave was filled with 0.25 g of 1-(2,2-dimethyl-4-propyl-1-quinolyl) ethanone (88.7% a/a HPLC, 1.02 mmol, 1 equiv), 7.8 mg of catalyst (Va-1) (5 μmol, 0.5 mol %) and 5 mL of 1,1,1,3,3,3-hexafluoro-2-propanol. The autoclave was pressurized with argon three times, followed by pressurization with hydrogen twice. Subsequently, the autoclave was pressurized with 60 bar of hydrogen, heated to 85° C. and the reaction mixture was stirred at that temperature for 15 h. Chromatographic analysis of the cooled and de-pressurized reaction mixture showed 92.4% a/a HPLC conversion of starting material to the hydrogenated product 1-(2,2-dimethyl-4-propyl-3,4-dihydroquinolin-1-yl) ethanone with an enantioselectivity of 81.2% ee.

Example 6: Comparison Using Reaction Conditions from Example 6 of DE112015001290 T5

A 25 mL autoclave was filled with 0.5 g of 1-(2,2,4-trimethyl-1-quinolyl) ethanone (2.3 mmol, 1 equiv), 43.9 mg of catalyst (Va-1) (29 μmol, 1.2 mol %) and 12.2 mL of 2,2,2-trifluoroethanol. The autoclave was pressurized with argon three times, followed by pressurization with hydrogen twice. Subsequently, the autoclave was pressurized with 70 bar of hydrogen, heated to 90° C. and the reaction mixture was stirred at that temperature for 9 h. Chromatographic analysis of the cooled and de-pressurized reaction mixture showed 70% a/a HPLC conversion of starting material to the hydrogenated product 1-[2,2,4-trimethyl-3,4-dihydroquinolin-1-yl]ethanone with an enantioselectivity of 95.5% ee.

Example 7: Comparison Using Catalyst from Example 6 of DE112015001290 T5

In the comparative example 7 the following commercially available Cy-UbaPHOX (CAS 583844-38-6) catalyst was used:

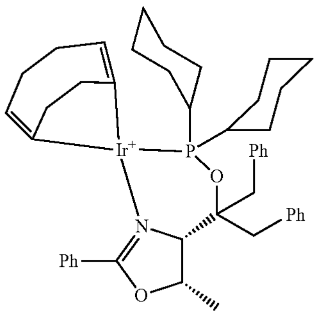

-continued

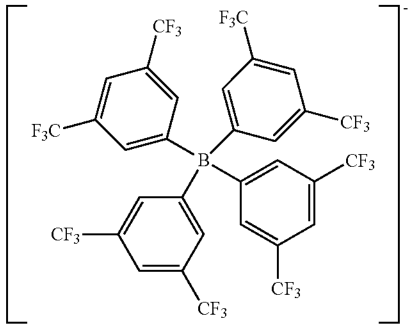

A 16 mL autoclave was filled with 0.7 g of 1-(2,2,4-trimethyl-1-quinolyl) ethanone (3.3 mmol, 1 equiv), 5.6 mg of catalyst (Cy-UbaPHOX, CAS 880262-14-6) (3.3 μmol, 0.1 mol %) and 4.2 mL of 1,1,1,3,3,3-hexafluor-2-propanol. The autoclave was pressurized with argon three times, followed by pressurization with hydrogen twice. Subsequently, the autoclave was pressurized with 60 bar of hydrogen, heated to 85° C. and the reaction mixture was stirred at that temperature for 16 h. Chromatographic analysis of the cooled and de-pressurized reaction mixture showed 84% a/a HPLC conversion of starting material to the hydrogenated product 1-[2,2,4-trimethyl-3,4-dihydroquinolin-1-yl]ethanone with an enantioselectivity of 81.7% ee.

Conclusion from comparative examples 6 and 7: Both the catalyst VI-a used in this invention (e.g. example 2) and the reaction conditions are superior to the benchmark catalyst and conditions from DE112015001290 T5 (example 6). For optimal results, the reaction conditions and the catalysts (e.g. Va-1) of this invention have to be used in combination (e.g. example 2). Other catalysts from this invention like Va-4, Va-6, Va-8, Va-10 and Va-22 show even superior activity to both Va-1 and Cy-UbaPHOX.

Detailed Comparison of experiments with DE112015001290 T5:

| Example | Catalyst | Catalyst [mol %] | Solvent | Conv. [%] | ee [%] |
|---|---|---|---|---|---|
| DE112015001290 T5, example 6 | Ir catalyst (I) | 1.2 | Trifluoro-ethanol | 14.3 | 31.3 |
| Present invention, example 6 | Va-1 | 1.2 | Trifluoro-ethanol | 70 | 95.5 |

The comparison shows that catalyst Va-1 of this invention is superior conversion and enantiomeric excess (ee) to Ir catalyst (I) from DE112015001290 T5 (example 6) under the conditions used in DE112015001290 T5, example 6 (1.2 mol % of catalyst in trifluoroethanol).

| Example | Catalyst | Catalyst [mol %] | Solvent | Conv. [%] | ee [%] |
|---|---|---|---|---|---|
| Present invention, example 7 | Ir catalyst (I) | 0.1 | Hexafluoroiso-propanol | 84 | 81.7 |
| Present invention, example 2 | Va-1 | 0.1 | Hexafluoroiso-propanol | 100 | 97.5 |

The comparison shows that catalyst Va-1 of this invention is superior in conversion and enantiomeric excess (ee) to Ir catalyst (I) from DE112015001290 T5, example 6 under the conditions used in the present patent application (0.1 mol % of catalyst in hexafluoroisopropanol).

Additionally, the conditions used in the present patent application (0.1 mol % of catalyst in hexafluoroisopropanol) are superior in conversion, enantiomeric excess (ee) and catalyst amount to the conditions used in DE112015001290 T5, example 6 (1.2 mol % of catalyst in trifluoroethanol).

Examples 8-11

Under an inert gas atmosphere, one well of a 96 well-plate autoclave was filled with 9.8 mg of 1-(2,2,4-trimethyl-1-quinolyl)ethanone (45.5 μmol, 1 equiv) and 1.82 μmol of catalyst (4 mol %, see table 1) in 0.49 mL of 2,2,2-trifluoroethanol. The autoclave was pressurized with 30 bar of hydrogen, heated to 40° C. and the reaction mixture was shaken at that temperature for 16 h. Chromatographic analysis of the cooled and de-pressurized reaction mixture showed the % a/a HPLC conversion rates of starting material to the hydrogenated product 1-[2,2,4-trimethyl-3,4-dihydroquinolin-1-yl]ethanone. The % a/a HPLC conversion rates and enantioselectivities are depicted in table 1 below.

| Ex. | Catalyst[1)] | Ligand L* | Anion Y | Conversion (% a/a HPLC) | % ee |
|---|---|---|---|---|---|
| 8 | [IrL*(COD)]Y | 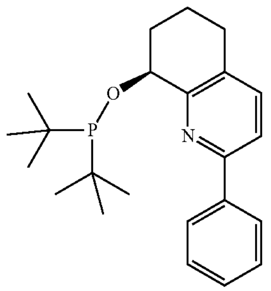 [SMILES: CC(C)(C)P(O[C@H]1CCCc2ccc(-c3ccccc3)nc21)C(C)(C)C] | BARF[2)] | 47 | 89 |
| 9 | [IrL*(COD)]Y | 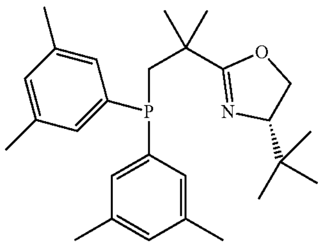 [SMILES: Cc1cc(C)cc(P(CC(C)(C)C2=N[C@@H](C(C)(C)C)CO2)c2cc(C)cc(C)c2)c1] | BARF[2)] | 47 | 93 |
| 10 | [IrL*(COD)]Y | 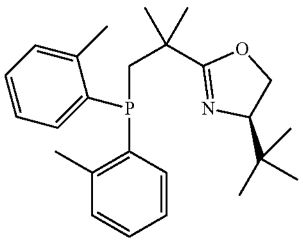 [SMILES: Cc1ccccc1P(CC(C)(C)C1=N[C@H](C(C)(C)C)CO1)c1ccccc1C] | BARF[2)] | 55 | 91 |
| 11 | [IrL*(COD)]Y | 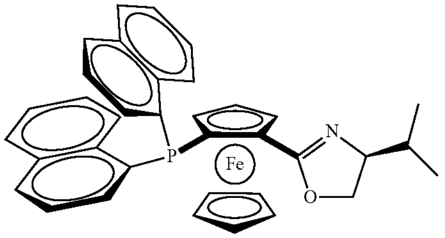 | BARF[2)] | 44 | 51 |

[1)]The catalyst used in example 8 was prepared according to the method disclosed in S. Kaiser et al., Angew. Chem. Int. Ed. 2006, 45, 5194-5197; the catalysts used in examples 9 and 10 were prepared according to the method disclosed in W. J. Drury III et al., Angew. Chem. Int. Ed. 2004, 43, 70-74; the catalyst used in example 11 was formed in situ from $[Ir(COD)_2]BARF$ and the depicted ligand.
[2)]BARF = Tetrakis[3,5-bis(trifluoromethyl)phenyl]borate

Examples 12-39

The Ir-complex (catalyst loading given) and 0.64 g 1-(2,2,4-trimethyl-1-quinolyl) ethanone (3 mmol) were placed in an 8-mL autoclave vial containing a PTFE-coated stirring bar. The autoclave vial was closed using a screw cap with septum and flushed with argon (10 min). Hexafluoroisopropanol (HFIP, 4 mL) was added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the vial was taken out of the autoclave and the reactions outcome was determined by GC-FID analysis (deluted with EtOH) and the enantiomeric excess by HPLC analysis.

| Example | Catalyst | Reaction time (h) | catalyst loading (mol %) | Conversion GC (% a/a) | Enantiomeric excess (% ee) |
|---|---|---|---|---|---|
| 12 | Va-1 | 16 | 0.1 | 99.2 | 98.0 |
| 13 | Va-1 | 6 | 0.1 | 81.5 | 97.5 |
| 14 | Va-2 | 6 | 0.1 | 94.5 | 97.5 |
| 15 | Vb-3 | 6 | 0.05 | 88.2 | 97.6 |
| 16 | Va-4 | 16.5 | 0.05 | 94.4 | 97.3 |
| 17 | Va-4 | 16 | 0.1 | 99.4 | 96.0 |
| 18 | Va-4 | 16.5 | 0.1 | 92.0 | 97.0 |
| 19 | Vb-5 | 16 | 0.05 | 98.4 | 96.8 |
| 20 | Vb-5 | 6 | 0.025 | 67.2 | 97.3 |
| 21 | Va-6 | 6 | 0.025 | 91.6 | 97.3 |
| 22 | Vb-7 | 16.5 | 0.05 | 98.9 | 95.8 |
| 23 | Vb-7 | 16.5 | 0.025 | 79.5 | 97.5 |
| 24 | Va-8 | 16 | 0.025 | 94.1 | 97.5 |
| 25 | Va-9 | 16.5 | 0.025 | 81.7 | 97.9 |
| 26 | Va-10 | 16.5 | 0.025 | 98.0 | 98.1 |
| 27 | Va-11 | 16.5 | 0.025 | 42.2 | 94.5 |
| 28 | Va-12 | 16 | 0.05 | 92.4 | 96.9 |
| 29 | Va-13 | 16.5 | 0.1 | 91.2 | 97.0 |
| 30 | Va-14 | 16 | 0.05 | 64.7 | 92.4 |
| 31 | Va-15 | 16 | 0.05 | 34.6 | 83.2 |
| 32 | Va-16 | 16 | 0.05 | 87.9 | 95.8 |
| 33 | Vb-17 | 16 | 0.1 | 30 | 90.0 |
| 34 | Va-18 | 16 | 0.1 | 76.0 | 96.0 |
| 35 | Va-19 | 16 | 0.025 | 7.2 | 70.8 |
| 36 | Va-20 | 16 | 0.025 | 60 | 92.1 |
| 37 | Va-21 | 16 | 0.025 | 74 | 98.0 |
| 38 | Va-22 | 1 | 0.025 | 97.5 | 97.3 |
| 39 | Va-23 | 16 | 0.1 | 30 | 94 |

The invention claimed is:

1. A process for preparing a compound of the formula (Ia) or (Ib), (Ia)

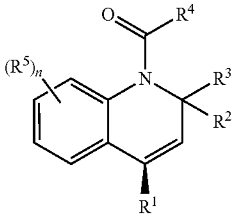

(Ib)

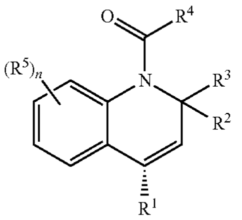

wherein $R^1$ is $C_1$-$C_6$-alkyl, $R^2$ and $R^3$ are the same and are selected from the group consisting of $C_1$-$C_6$-alkyl, $R^4$ is $C_1$-$C_6$-alkyl, n is 0 or 1, each substituent $R^5$, if present, is independently selected from the group consisting of halogen, comprising enantioselective hydrogenation of a compound of the formula (II)

(II)

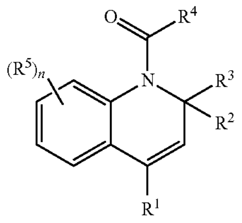

wherein the substituents $R^1$, $R^2$, $R^3$, $R^4$, $R^5$ and the integer n are each as defined for the compound of the formula (Ia) or (Ib), in presence of a chiral iridium catalyst, characterized in that the chiral iridium catalyst comprises a chiral ligand of the formula (IIIa) or (IIIb)

(IIIa)

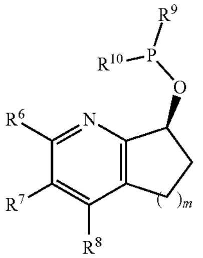

(IIIb)

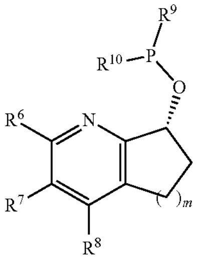

wherein $R^6$ and $R^7$ are independently from one another selected from consisting of hydrogen, $C_1$-$C_6$-alkyl, and $C_6$-$C_{14}$-aryl, wherein the $C_6$-$C_{14}$-aryl is optionally substituted by one to five substituents selected from the group consisting of halogen, $C_1$-$C_4$-alkyl, $C_1$-$C_4$-haloalkyl, and $C_1$-$C_4$-alkoxy, $R^8$ is methyl, $R^9$ and $R^{10}$ are independently from one another selected from the group consisting of $C_1$-$C_6$-alkyl, and $C_3$-$C_{12}$-cycloalkyl, and m is 1 or 2.

2. The process according to claim 1, wherein $R^2$ and $R^3$ are the same and are selected from $C_1$-$C_4$-alkyl, and $R^4$ is $C_1$-$C_4$-alkyl.

3. The process according to claim 1, wherein $R^1$ is methyl, ethyl or n-propyl, $R^2$ and $R^3$ are methyl, and $R^4$ is $C_1$-$C_4$-alkyl.

4. The process according to claim 1, wherein the chiral iridium catalyst comprises a chiral ligand of the formula (IIIa) or (IIIb), wherein $R^6$ is $C_6$-$C_{14}$-aryl, wherein the $C_6$-$C_{14}$-aryl is unsubstituted or substituted by one to five substituents selected from the group consisting of halogen, $C_1$-$C_4$-alkyl, $C_1$-$C_4$-haloalkyl, and $C_1$-$C_4$-alkoxy, $R^7$ is selected from the group consisting of hydrogen, and $C_1$-$C_6$-alkyl, and $R^9$ and $R^{10}$ are independently from one another selected from the group consisting of $C_1$-$C_6$-alkyl, and $C_3$-$C_{12}$-cycloalkyl.

5. The process according to claim 1, wherein the chiral iridium catalyst comprises a chiral ligand of the formula (IIIa) or (IIIb), wherein $R^6$ is selected from the group consisting of 1-naphtyl, 2-naphtyl, 9-antracenyl, 9-phenantryl or phenyl, which is unsubstituted or substituted by one to five substituents selected from the group consisting of halogen, $C_1$-$C_4$-alkoxy, $C_1$-$C_4$-alkyl, and $C_1$-$C_4$-haloalkyl, $R^7$ is hydrogen or $C_1$-$C_6$-alkyl, and $R^9$ and $R^{10}$ are independently from one another selected from the group consisting of ethyl, iso-propyl, sec-butyl, iso-butyl, tert-butyl, cyclohexyl, cyclopentyl, and adamantyl.

6. The process according to claim 1, wherein the hydrogenation is conducted using hydrogen gas at a pressure of from 1 to 300 bar.

7. The process according to claim 1, wherein the amount of iridium catalyst used is within the range of from 0.001 mol % to 5 mol %, based on the amount of the compound of the formula (II).

8. The process according to claim 1, wherein the hydrogenation is conducted at a temperature within the range of from 20° C. to 130° C.

9. The process according to claim 1, wherein the hydrogenation is conducted in presence of a solvent selected from the group consisting of 2,2,2-trifluoroethanol, 1,1,1,3,3,3-hexafluoro-2-propanol, 1,2-dichloroethane, tetrafluoropropanol, and mixtures thereof.

10. The process according to claim 1, wherein the chiral iridium catalyst has the formula (Va), or (Vb):

(Va)

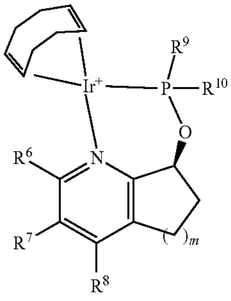

$[B(R^{18})_4]^-$

-continued (Vb)

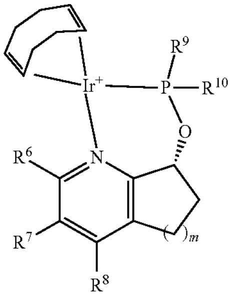

$[B(R^{18})_4]^-$ wherein $R^6$ is selected from the group consisting of 1-naphtyl, 2-naphtyl, 9-antracenyl, 9-phenantryl or phenyl, wherein 1-naphtyl, 2-naphtyl, 9-antracenyl, 9-phenantryl and phenyl are unsubstituted or substituted by one to five substituents selected from the group consisting of halogen, $C_1$-$C_4$-alkoxy, $C_1$-$C_4$-alkyl, and $C_1$-$C_4$-haloalkyl, $R^7$ is hydrogen or $C_1$-$C_6$-alkyl, $R^8$ is methyl, $R^9$ and $R^{10}$ are independently from one another selected from the group consisting of ethyl, iso-propyl, sec-butyl, iso-butyl, tert-butyl, cyclohexyl, cyclopentyl, and adamantyl, and $R^{18}$ is phenyl, which is unsubstituted or substituted with one to five substituents selected from group consisting of fluorine and $C_1$-$C_4$-haloalkyl.

11. The process according to claim 10, wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl 2,4,6-triisopropylphenyl, 9-phenantryl or 2,6-diethyl-4-methylphenyl, $R^7$ is hydrogen, and $R^9$ and $R^{10}$ are each the same and tert-butyl, adamantly, cyclopentyl or cyclohexyl.

12. The process according to claim 1, wherein the chiral iridium catalyst comprises a chiral ligand of the formula (IIIa) or (IIIb), wherein $R^6$ is selected from the group consisting of 1-naphtyl, 2-naphtyl, 9-antracenyl, 9-phenantryl or phenyl, which is unsubstituted or substituted by one to five substituents selected from the group consisting of halogen, $C_1$-$C_4$-alkoxy, $C_1$-$C_4$-alkyl, $C_1$-$C_4$-haloalkyl and phenyl, wherein the phenyl again is unsubstituted or substituted by one to five $C_1$-$C_6$-alkyl substituents, $R^7$ is hydrogen or $C_1$-$C_6$-alkyl, and $R^9$ and $R^{10}$ are independently from one another selected from the group consisting of ethyl, iso-propyl, sec-butyl, iso-butyl, tert-butyl, cyclohexyl, cyclopentyl, and adamantyl.

13. The process according to claim 12, wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl 2,4,6-triisopropylphenyl, 9-phenantryl or 2,6-diethyl-4-methylphenyl, $R^7$ is hydrogen $R^9$ and $R^{10}$ are each the same and tert-butyl, cyclopentyl or cyclohexyl, and m is 1.

14. The process according to claim 1, wherein the chiral iridium catalyst comprises a chiral ligand of the formula (IIIa) or (IIIb), wherein $R^6$ is selected from the group consisting of phenyl, 2,6- or 3,5-dimethylphenyl, 2,4,6-trimethylphenyl, 4-tert-butylphenyl, 4-methoxyphenyl, 3,5-bis-tert-butyl-4-methoxyphenyl, 4-tert-butyl-2,6-dimethylphenyl, 4-fluorophenyl, 4-trifluoromehtylphenyl, 1-naphtyl, 9-antracenyl, 2,4,6-triisopropylphenyl, 9-phenantryl and 2,6-diethyl-4-methylphenyl, $R^7$ is hydrogen, $R^9$ and $R^{10}$ are independently from one another selected from the group consisting of ethyl, iso-propyl, sec-butyl, iso-butyl, tert-butyl, cyclohexyl, cyclopentyl, and adamantyl, and m is 1.

* * * * *